United States Patent
Sampson et al.

(10) Patent No.: US 9,974,848 B2
(45) Date of Patent: May 22, 2018

(54) TETANUS TOXOID AND CCL3 IMPROVE DC VACCINES

(71) Applicant: Duke University, Durham, NC (US)

(72) Inventors: John H. Sampson, Durham, NC (US); Duane A. Mitchell, Durham, NC (US); Kristen A. Batich, Durham, NC (US); Michael D. Gunn, Durham, NC (US)

(73) Assignee: Duke University, Durham, NC (US)

( * ) Notice: Subject to any disclaimer, the term of this patent is extended or adjusted under 35 U.S.C. 154(b) by 0 days. days.

(21) Appl. No.: 15/036,878

(22) PCT Filed: Nov. 14, 2014

(86) PCT No.: PCT/US2014/065666
§ 371 (c)(1),
(2) Date: May 16, 2016

(87) PCT Pub. No.: WO2015/073801
PCT Pub. Date: May 21, 2015

(65) Prior Publication Data
US 2016/0271240 A1    Sep. 22, 2016

Related U.S. Application Data

(60) Provisional application No. 61/904,250, filed on Nov. 14, 2013.

(51) Int. Cl.
| | | |
|---|---|---|
| *A61K 39/08* | (2006.01) | |
| *A61K 39/39* | (2006.01) | |
| *A61K 38/19* | (2006.01) | |
| *A61K 39/00* | (2006.01) | |
| *A61K 39/05* | (2006.01) | |
| *A61K 39/09* | (2006.01) | |
| *A61K 39/102* | (2006.01) | |
| *A61K 39/12* | (2006.01) | |
| *A61K 49/00* | (2006.01) | |
| *A61K 49/06* | (2006.01) | |
| *C07K 14/285* | (2006.01) | |
| *C07K 14/315* | (2006.01) | |
| *C07K 14/33* | (2006.01) | |
| *C07K 14/34* | (2006.01) | |
| *C07K 14/47* | (2006.01) | |
| *C07K 14/52* | (2006.01) | |
| *C12N 7/00* | (2006.01) | |

(52) U.S. Cl.
CPC ............ *A61K 39/08* (2013.01); *A61K 38/195* (2013.01); *A61K 39/0011* (2013.01); *A61K 39/05* (2013.01); *A61K 39/092* (2013.01); *A61K 39/102* (2013.01); *A61K 39/12* (2013.01); *A61K 39/39* (2013.01); *A61K 49/0008* (2013.01); *A61K 49/06* (2013.01); *C07K 14/285* (2013.01); *C07K 14/3156* (2013.01); *C07K 14/33* (2013.01); *C07K 14/34* (2013.01); *C07K 14/4748* (2013.01); *C07K 14/523* (2013.01); *C12N 7/00* (2013.01); *A61K 2039/5154* (2013.01); *A61K 2039/5158* (2013.01); *A61K 2039/53* (2013.01); *A61K 2039/54* (2013.01); *A61K 2039/545* (2013.01); *A61K 2039/55544* (2013.01); *A61K 2039/58* (2013.01); *A61K 2039/585* (2013.01); *A61K 2039/70* (2013.01); *C07K 2319/55* (2013.01); *C12N 2710/16134* (2013.01); *C12N 2710/16171* (2013.01)

(58) Field of Classification Search
None
See application file for complete search history.

(56) References Cited

U.S. PATENT DOCUMENTS

| | | | | |
|---|---|---|---|---|
| 2006/0045881 A1* | 3/2006 | Molldrem | .......... | A61K 39/0011 424/178.1 |
| 2009/0081202 A1 | 3/2009 | Fischer et al. | | |

FOREIGN PATENT DOCUMENTS

| | | |
|---|---|---|
| WO | 97-28273 A1 | 8/1997 |
| WO | 03-035105 A2 | 5/2003 |
| WO | 2007-071692 A2 | 6/2007 |

OTHER PUBLICATIONS

Gindler et al. (CDC Recommended childhood immunization schedule, MMWR 44:RR-5, 1995).*
Hinman et al. (CDC Recommendations of the Advisory Committee on Immunization Practices (ACIP): Use of Vaccines and Immune Globulins in Persons with Altered Immunocompetence, MMWR 42:RR-4, 1993).*
International Search Report, PCT/US2014/065666, dated Mar. 11, 2015.

(Continued)

*Primary Examiner* — Brian Gangle
(74) *Attorney, Agent, or Firm* — Banner & Witcoff, LTD.

(57) ABSTRACT

Pre-conditioning a vaccine site with a potent recall antigen such as tetanus/diphtheria (Td) toxoid can significantly improve the lymph node homing and efficacy of tumor antigen-specific DC vaccines. Patients given Td had enhanced DC migration bilaterally and significantly improved survival. In mice, Td pre-conditioning also enhanced bilateral DC migration and suppressed tumor growth in a manner dependent on the chemokines CCL3 and CCL21 and Td-activated $CD4^+$ T cells. Interference with any component of this axis markedly reduced Td-mediated DC migration and antitumor responses. Our clinical studies and corroborating investigations in mice suggest that preconditioning with a potent recall antigen represents a viable strategy to increase DC homing to lymph nodes and improve antitumor immunotherapy.

31 Claims, 16 Drawing Sheets

(56) References Cited

OTHER PUBLICATIONS

Martin-Fontecha, Alfonso et al., 'Regulation of dendritic cell migration to the draining lymph node: impace on T lymphocyte traffic and priming', J. Exp. Med., Aug. 18, 2003, vol. 198, No. 4, pp. 615-621.

* cited by examiner

| PATIENT | SEX | AGE | RACE | KPS | WHO PERFORMANCE STATUS | MMSE | IDH1 | MGMT STATUS | MGMT PROMOTER METHYLATION | VACCINE SITE PRE-CON-DITIONING | PFS (RANDOMI-ZATION) | OS (RAN-DOMI-ZATION) | PFS (DIAGNOSIS) | OS (DIAGNOSIS) | EORTC PREDICTED MEDIAN OS | EORTC O-E | RPA CLASS | RPA O-E |
|---|---|---|---|---|---|---|---|---|---|---|---|---|---|---|---|---|---|---|
| 1 | F | 46 | W | 100 | 0 | 29 | - | N/A | N/A | Td | 8.8 | 19.2 | 15.4 | 25.7 | 26.8* | -1.1 | III | 7.8 |
| 2 | F | 32 | W | 100 | 0 | 29 | + | - | - | DC | 21.7 | 35.2 | 27.8 | 41.3 | 13.0¶ | 28.3¶ | III | 23.4 |
| 3 | M | 62 | W | 90 | 1 | 29 | - | - | - | DC | 4.9 | 10.9 | 11.2 | 17.3 | 9.8 | 7.5 | IV | 6.2 |
| 4 | M | 71 | W | 90 | 1 | 30 | - | - | + | Td | 41.4 | 41.4 | 47.3† | 47.3† | 16.4 | 30.9 | IV | 36.2 |
| 5 | M | 43 | W | 90 | 1 | 28 | - | - | + | DC | 2.5 | 12.2 | 10.0 | 19.7 | 16.4 | 3.3 | IV | 1.8 |
| 6 | F | 59 | W | 80 | 1 | 30 | - | - | - | Td | 39.5 | 39.5 | 45.0† | 45.0† | 9.8 | 35.2 | III | 33.9 |
| 7 | M | 75 | W | 90 | 1 | 26 | - | - | + | Td | 9.5 | 14.7 | 15.4 | 20.6 | 11.8 | 8.8 | IV | 9.5 |
| 8 | F | 58 | W | 90 | 1 | 22 | - | + | - | DC | 2.5 | 13.4 | 9.1 | 20.0 | 13.1* | 6.9 | IV | 8.9 |
| 9 | M | 30 | H | 90 | 1 | 29 | N/A | + | N/A | Td | 36.6 | 36.6 | 44.1† | 44.1† | 21.3* | 22.8 | III | 26.2 |
| 10 | F | 66 | W | 80 | 1 | 24 | - | + | - | DC | 3.9 | 9.5 | 10.4 | 16.0 | 6.9 | 9.1 | IV | 4.9 |
| 11 | F | 28 | W | 100 | 0 | 28 | - | - | - | DC | 6.1 | 7.4 | 12.5 | 13.8 | 13.0 | 0.8 | III | 4.1 |
| 12 | M | 59 | W | 90 | 1 | 29 | S | S | S | DC | S | S | 5.1 | 19.0 | 18.1** | 0.9 | IV | 7.9 |
| 13 | M | 71 | W | 90 | 1 | 21 | - | + | + | Td | 12.7 | 15.2 | 18.5 | 20.9 | 11.8 | 9.1 | IV | 9.8 |
| MEDIAN DC | | 58.5 | | 90 | 1 | 28 | | | | | 4.4 | 11.6 | 10.8 | 18.5 | 13.0¶ | 6.9¶ | IV | 6.2 |
| MEDIAN Td | | 65 | | 90 | 1 | 29 | | | | | >36.6 | >36.6 | >36.6 | >36.6 | 14.1 | >16 | IV | >16 |

TETANUS TOXOID AND CCL3 IMPROVE DC VACCINES

This invention was made with government support under P50CA108786, P50-NS20023, R01-CA177476-01, R01-NS067037, P01-CA154291-01A1, P50-NS020023-30, 1UL2 RR024128-01 awarded by National Institutes of Health. The government has certain rights in the invention.

TECHNICAL FIELD OF THE INVENTION

This invention is related to the area of immunotherapy. In particular, it relates to cancer immunotherapy.

BACKGROUND OF THE INVENTION

Upon stimulation, dendritic cells (DCs) mature and migrate to draining lymph nodes to induce immune responses against pathogens[1]. As such, autologous, mature DCs generated ex vivo have been pulsed with tumor antigens and injected back into patients as a form of antitumor immunotherapy. While DC vaccines have shown limited promise in the treatment of patients with advanced cancers[2-4] including glioblastoma (GBM),[5-7] the factors dictating DC vaccine efficacy remain poorly understood. There is a continuing need in the art to improve DC vaccine efficacy as well as other types of vaccines' efficacy.

SUMMARY OF THE INVENTION

A method of immunizing a human is provided. A first acellular immunogen is administered intradermally to the human A second immunogen is administered intradermally to the human Administration of the first immunogen increases migration of the second immunogen to vaccine draining lymph nodes (VDLNs). The first acellular immunogen is not an inflammatory cytokine. The first and second immunogens are distinct. The human has been previously immunized with or exposed to the first immunogen, such that the human has memory T cells which are specific and responsive to the first immunogen.

A fusion protein is provided. It comprises tetanus toxoid and chemokine CCL3; diphtheria toxoid and chemokine CCL3; tetanus toxoid and a tumor specific or tumor associated antigen; tetanus toxoid and an antigen of an infectious agent; diphtheria toxoid and a tumor specific or tumor associated antigen; diphtheria toxoid and an antigen of an infectious agent; chemokine CCL3 and a tumor specific antigen; or chemokine CCL3 and an antigen of an infectious agent.

A pharmaceutical composition is provided. It comprises tetanus toxoid and chemokine CCL3; diphtheria toxoid and chemokine CCL3; tetanus toxoid and a tumor specific or tumor associated antigen; tetanus toxoid and an antigen of an infectious agent; diphtheria toxoid and a tumor specific or tumor associated antigen; diphtheria toxoid and an antigen of an infectious agent; chemokine CCL3 and a tumor specific antigen; or chemokine CCL3 and an antigen of an infectious agent.

A kit is provided. The kit comprises a first acellular immunogen and a second immunogen for intradermal administration to a human. The first acellular immunogen is selected from the group consisting of tetanus toxoid, diphtheria toxoid, and tetanus-diphtheria toxoids. The second immunogen is selected from the group consisting of a tumor-associated, a tumor-specific antigen, an antigen of an infectious agent, a dendritic cell vaccine, an antigen-pulsed dendritic cell vaccine, and dendritic cells pulsed with a CMV integument protein pp65 RNA.

Another method of immunizing a human is provided. Chemokine CCL3 is administered to the human. An immunogen is administered intradermally to the human. Administration of chemokine CCL3 increases migration of the immunogen to vaccine draining lymph nodes VDLNs).

Another kit is provided which comprises components for administration to a human. The components comprise chemokine CCL3; and an immunogen selected from the group consisting of a tumor-associated, a tumor-specific antigen, an antigen of an infectious agent, a dendritic cell vaccine, an antigen-pulsed dendritic cell vaccine, and dendritic cells pulsed with a CMV integument protein pp65 RNA.

A pharmaceutical composition is provided that comprises chemokine CCL3 and an immunogen selected from the group consisting of a tumor-associated, a tumor-specific antigen, an antigen of an infectious agent, a dendritic cell vaccine, an antigen-pulsed dendritic cell vaccine, and dendritic cells pulsed with a CMV integument protein pp65 RNA.

These and other embodiments which will be apparent to those of skill in the art upon reading the specification provide the art with methods and products for treating infectious diseases and neoplastic diseases.

BRIEF DESCRIPTION OF THE DRAWINGS

FIG. 1a, Increased DC migration at 48 hours in patients randomized to Td (n=6) compared to unpulsed DCs (n=6) (*P=0.049). All errors, s.e.m. FIG. 1b, PFS and FIG. 1c, OS for Td and DC patients (**P=0.013). FIG. 1d and FIG. 1e, Hazard ratios (HRs): DC migration efficiency from both Td and DC cohorts showing the effect of a 1 unit increase in percent migration on PFS and OS (Cox proportional hazards model, HR=0.845 *P=0.027 for PFS; HR=0.820 *P=0.023 for OS). Three Td patients who did not progress and were alive at the time of survival analysis were censored and lived >36.6 months.

FIG. 2a, DC migration to inguinal and popliteal lymph nodes. Control inguinal vs. Td inguinal (*** P=0.0001); Td popliteal vs. Td inguinal, *P=0.014). FIG. 2b. DC migration in mice primed and boosted with saline (Primary Td) or Td (Control and Recall Td) and pre-conditioned with either Td (Primary and Recall Td) or saline (Control) (P=0.004; Control vs. Recall Td (P=0.006); Primary Td vs. Recall Td. P=0.011). FIG. 2c, DC migration to VDLNs in depleted Td-immunized mice (*P<0.0001: Td vs. CD4, P=0.005; Td vs. CD8, CD19, or NK11.1, P>0.05). FIG. 2d, DC migration following adoptive Td-activated CD4$^+$ T cell transfer (*P<0.0001; CD4$_{Act}$ vs. CD4$_{Naive}$, *P<0.05; Control vs. CD4$_{Naive}$, P>0.05; Td vs. CD4$_{Act}$, P>0.05). FIG. 2e, DC migration to lymph nodes contralateral and ipsilateral to pre-conditioning site; Top: human (P=0.28; n=6 per group). Bottom: mouse (P=0.37; n=6 per group,). FIG. 2f, Bilateral DC migration following Td-activated CD4$^+$ T cell transfer (CD4$_{Act}$ ipsilateral vs. contralateral, P=0.41). FIG. 2a-d, e (bottom), FIG. 2f, representative of four experiments. All figures show mean values±s.e.m. (n=at least 4 for all groups, n=at least 3 for GFP$^-$ groups).

FIG. 3a, Fold increase over mean of non-Td cohorts (patient and mouse CCL3, *P=0.031 and *P=0.039). FIG. 3b, CCL3 production in skin following Td pre-conditioning (Td ipsilateral vs. contralateral, ***P<0.0001, n=4 per group). FIG. 3c, CCL3 production following Td recall response (Recall Td vs. Primary Td, *P=0.02, n=4 per group). FIG. 3d, CCL3 dependence on presence of Td-activated CD4$^+$ T cells (Recall Td vs. Recall Td+αCD4, **P=0.01, n=4 per group). FIG. 3e, DC migration after Td pre-conditioning in Ccl3−/− hosts (wild-type vs. Ccl3−/−, *P=0.023, n=5 per group). FIG. 3f, Td-activated CD4$^+$ T cells fail to recapitulate increased DC migration in CCL3-deficient hosts (wild-type vs. Ccl3−/−, *P=0.029, n=4 per group). FIG. 3g, Limited DC migration rescued with CCL3 administration and established Td recall responses (n=4 per group). FIG. 3h, Restoration of skin-derived CCL21 following Td pre-conditioning in Ccl3−/− hosts with CCL3 and Td recall response (All two group comparisons, n=4 per group). FIG. 3i, Bilateral lymph node CCL21 levels in wild-type inguinal lymph nodes following Td recall (ipsilateral, **P=0.013; contralateral, *P=0.021, n=4 per group). FIG. 3j, Increased lymph node CCL21 in Ccl3−/− hosts following CCL3 reconstitution and induction of Td recall response (All two group comparisons, n=4 per group). Representative of three experiments. Mean values±s.e.m.; intradermal (i.d.); intramuscular (i.m.); intravenous (i.v.).

FIG. 4a, Tumor volumes over time. Insert: Transformed tumor growth curves for mixed linear effects model. Pairwise comparisons of regression line slopes (***P<0.0001). Day 22 tumor volume (Td+OVA-DC vs. Td+GFP-DC, *P=0.002). FIG. 4b, Tumor antigen-specific responses with Td pre-conditioning. Day 15 tumor volume (Td+OVA-DC+B16-OVA vs. Td+OVA-DC+B16, P=0.0004; Td+OVA-DC+B16-OVA vs. Saline+OVA-DC+B16-OVA, P=0.0002). Day 22 tumor volume (Td+OVA-DC+B16-OVA vs. Td+OVA-DC+B16, *P<0.0001). FIG. 4c, Lack of protection against tumor growth in Td pre-conditioned Ccl3$^{-/-}$ mice. Day 11 tumor volume (all groups, P=0.005). Day 27 tumor volume (Td+OVA-DC plt vs. Td+OVA-DC Ccl3$^{-/-}$, *P=0.042). FIG. 4d, Antitumor responses generated by Td pre-conditioning are dependent on CCL21 expression in VDLNs. Day 16 tumor volume (all groups, **P=0.004). Day 24 mean tumor volume (Td+OVA-DC plt vs. Td+OVA-DC Ccl3$^{-/-}$, *P<0.05). Representative of three experiments (n=at least 5 mice per group). All errors, s.e.m; autologous lymphocyte transfer (ALT).

FIG. 9a, DC migration to ipsilateral lymph nodes (**P=0.0018; saline i.d. vs. Td i.d., *P<0.05, saline i.d. vs. TNF-α, *P<0.05, saline i.d. vs DCs, *P<0.05; Td i.d. vs. TNF-α and Td i.d. vs. DCs, N.S; DCs vs. TNF-α, N.S.). FIG. 9b, DC migration to contralateral lymph nodes (**P=0.003; saline i.d. vs. DCs or TNF-α, P>0.05; Td i.d. vs. TNF-α, DCs, or saline i.d., *P<0.05). Representative of three experiments, n=4 per group.

FIG. 10a a, Serum Cytokine panel of patients following vaccine site pre-conditioning with Td or unpulsed DCs (IFN-γ and IL-4, *P<0.05, n=6 patients per group). FIG. 10a b, Similar panel in mice (All comparisons, P>0.05, n=at least 5 per group). FIG. 10a c, Patient serum chemokines following vaccine site pre-conditioning. Patient CCL2 and CCL3 in Td recall (Td, n=6) vs. Non-Td (unpulsed DC, n=5) (*P<0.05). FIG. 10a d, Murine CCL22, CCL7, and CCL3 in Td recall (Td, n=8) and Non-Td (saline, n=8) (*P<0.05).

FIG. 12a, Gating strategy used to quantify DC subsets in inguinal lymph nodes following skin pre-conditioning with Td (LC: Langerhans cells. MoDC: monocyte-derived DC). FIG. 12b, Day 8 migration of LC population to inguinal lymph nodes in Ccl3−/− hosts is reduced in absence of CCL3 (*P=0.046, two-sample t test). Representative of three experiments (n=4 per group).

FIG. 14 (Extended Data Table 1). Clinical trial patient characteristics. Demographic and prognostics factors of newly-diagnosed GBM patients with vaccine site pre-conditioning randomization strategy and corresponding PFS and OS from the time of surgery and from randomization to pre-conditioning. Observed and predicted survival times are expressed in months. Median values are shown for Td and unpulsed DC cohorts. Predicted median OS for RPA Class yielded 17.9 months for Class III and 11.1 months for Class IV based on Curran et al. recursive partition analysis. Model 3 of the EORTC Scoring System that incorporated MGMT promoter methylation status. MMSE score, and WHO Performance Status was used to generate predicted median survival rates.

Figures 1A, 1B, 1C, 1D, 1E:
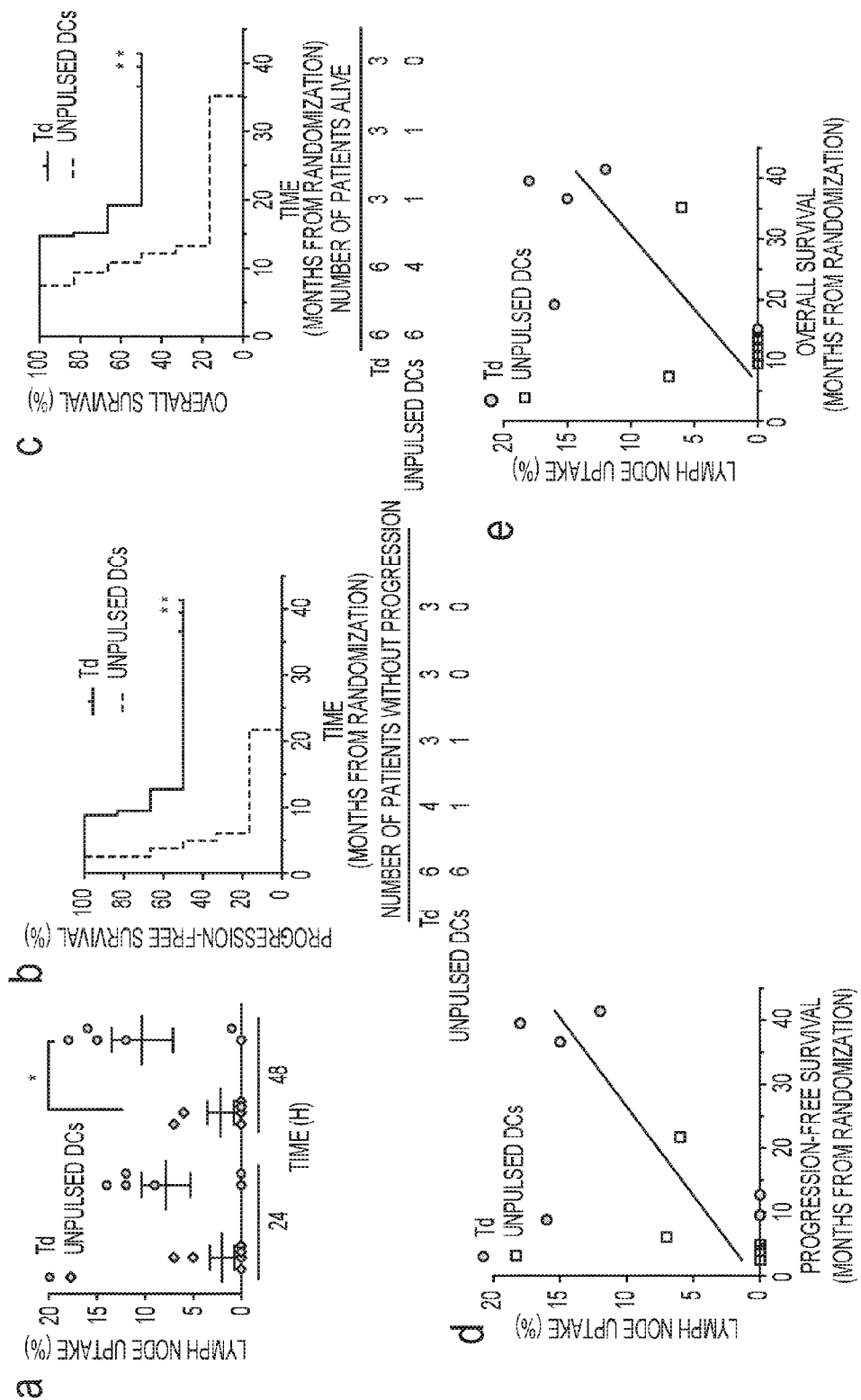
FIG. 1a-1e. Td pre-conditioning increases DC migration to VDLNs and is associated with improved clinical outcomes.

\* Model 2 of EORTC scoring system if methylation status unavailable

† No progression

‡ Alive

§ Patient progressed prior to time of randomization for vaccine site pre-conditioning KPS, Karnofsky Performance Status; WHO, World Health Organization; MMSE, Mini-Mental State Examination, IDH1, isocitrate dehydrogenase type 1; MGMT, $O^6$-Methylguanine-DNA methyltransferase; PFS, progression-free survival; OS, overall survival; EORTC, European Organization for Research and Treatment of Cancer; O-E, observed—expected survival months; RPA, recursive partitioning analysis; NA, tissue not available.

DETAILED DESCRIPTION OF THE INVENTION

The inventors have developed a method and reagents for increasing an immune response in a human or other mammal. This is particularly useful where an increased immune response is desirable, such as in an individual that that has a tumor or an individual that has an infectious disease.

If an immune response is desired to an antigen, such as a tumor-associated, a tumor-specific, a bacterial, a viral, a fungal, or a parasitic antigen, typically one will immunize or vaccinate with such an antigen, called here an immunogen, or a second immunogen. But often the immune response is found to be suboptimal. The inventors have found that a suboptimal immune response can be enhanced by pretreatment with another, apparently unrelated, immunogen, called here a first immunogen. The first immunogen may be acellular. Preferably the subject has been previously immunized with or exposed to the first immunogen and the human has memory T cells or antibodies which are specific and responsive to the first immunogen. The first immunogen may be an agent that is not an inflammatory cytokine. Treatment with the first immunogen may be anytime from at least 0, 0.1, 1, 2, 3, 4, 5, 6, 7, 8, 9, 10, 12 hours before the second immunogen is administered up until 24, 36, 48, 60, 72 hours, and up to 4, 5, 6, or 7 days, or even up to 1, 2, 3, or 4 weeks.

The first immunogen may be, for example, tetanus toxoid, diphtheria toxoid, tetanus-diphtheria toxoids, or any antigen which induces a CD4$^+$ T cell immune response. The first immunogen may be a fusion protein that comprises, for example, tetanus toxoid, diphtheria toxoid, or tetanus-diphtheria toxoids. The inventors, while not wishing to be bound by any theory or mechanism, have found that the first immunogen works by increasing the migration of the second immunogen to vaccine draining lymph nodes (VDLNs). Additionally, the increase in migration is dependent on the presence of chemokine CCL3. Administration of CCL3 or granulocyte-macrophage colony stimulating factor (GM-CSF) may be used to substitute or augment the effect of the first immunogen. Such administration may employ the chemokine or cytokine itself, or the chemokine or cytokine as part of a fusion protein with another entity, such as a first immunogen discussed above.

Administration of the first and/or second immunogens or agents may be via any convenient route. Intradermal, intravenous, subcutaneous, intramuscular, oral, sublingual, anal, or other delivery routes may be applied.

Tumors that are amenable to immunological therapy include, without limitation, glioblastoma, pilocytic astrocytomas, subependymal giant cell gliomas (WHO Grade I); diffuse astrocytomas, oligodendrogliomas, oligoastrocytomas, ependymomas, pleomorphic xanthoastrocytomas (WHO Grade II); anaplastic astrocytomas, anaplastic oligodendrogliomas, and anaplastic oligoastrocytomas (WHO Grade III); GBMs medulloblastomas (WHO Grade IV), lung cancers, gastric cancers, ovarian cancers, breast cancers, colorectal cancers, pancreatic cancers, prostate cancers, chronic myelogenous leukemias, chronic lymphocytic leukemias, acute lymphoblastic leukemias, and acute myelogenous leukemias.

Infectious agents that are amenable to the immunological therapy include without limitation bacterial, fungal, viral, and parasitic agents, such as protozoa and helminthes. Exemplary of such infectious agents are *Acinetobacter baumannii*; *Actinomyces israelii*; *Actinomyces gerencseriae*; *Propionibacterium propionicus*; *Trypanosoma brucei*; HIV (Human immunodeficiency virus); *Entamoeba histolytica*; *Anaplasma* genus; *Bacillus anthracis*; *Arcanobacterium haemolyticum*; Junin virus; *Ascaris lumbricoides*; *Aspergillus* genus; Astroviridae family; *Babesia* genus; *Bacillus cereus*; multiple bacteria; multiple bacteria; *Bacteroides* genus; *Balantidium coli*; *Baylisascaris* genus; BK virus; Piedraia hortae; *Blastocystis hominis*; *Blastomyces dermatitidis*; Machupo virus; *Borrelia* genus; *Clostridium botulinum*; *Sabia*; *Brucella* genus; the bacterial family Enterobacteriaceae; *Burkholderia cepacia* and other *Burkholderia* species; *Mycobacterium ulcerans*; Caliciviridae family; *Campylobacter* genus; *Candida albicans* and other *Candida* species; *Bartonella henselae*; Group A *Streptococcus* and *Staphylococcus*; *Trypanosoma cruzi*; *Haemophilus ducreyi*; Varicella zoster virus (VZV); Alphavirus; *Chlamydia trachomatis*; *Chlamydophila pneumoniae*; *Vibrio cholerae*; *Fonsecaea pedrosoi*; *Clonorchis sinensis*; *Clostridium difficile*; *Coccidioides immitis* and *Coccidioides posadasii*; Colorado tick fever virus (CTFV); rhinoviruses and coronaviruses; PRNP; Crimean-Congo hemorrhagic fever virus; *Cryptococcus neoformans*; *Cryptosporidium* genus; *Ancylostoma braziliense*; multiple other parasites; *Cyclospora cayetanensis*; *Taenia solium*; Cytomegalovirus; Dengue viruses (DEN-1; DEN-2; DEN-3 and DEN-4)—Flaviviruses; *Dientamoeba fragilis*; *Corynebacterium diphtheriae*; *Diphyllobothrium*; *Dracunculus medinensis*; Ebolavirus (EBOV); *Echinococcus* genus; *Ehrlichia* genus; *Enterobius vermicularis*; *Enterococcus* genus; Enterovirus genus; *Rickettsia prowazekii*; Parvovirus B19; Human herpesvirus 6 (HHV-6) and Human herpesvirus 7 (HHV-7); *asciolopsis buski*; *Fasciola hepatica* and *Fasciola gigantica*; PRNP; Filarioidea superfamily; *Clostridium erfringens*; *Fusobacterium* genus; *Clostridium perfringens*; other *Clostridium* species; *Geotrichum candidum*; *Giardia intestinalis*; Burkholderia mallei; *Gnathostoma spinigerum* and *Gnathostoma hispidum*; *Neisseria gonorrhoeae*; *Klebsiella granulomatis*; *Streptococcus pyogenes*; *Streptococcus agalactiae*; *Haemophilus influenzae*; Enteroviruses; mainly Coxsackie A virus and Enterovirus 71 (EV71); Sin Nombre virus; Heartland virus; *Helicobacter pylori*; *Escherichia coli* O157:H7; O111 and O104:H4; Bunyaviridae family; Hepatitis A Virus; Hepatitis B Virus; Hepatitis C Virus; Hepatitis D Virus; Hepatitis E Virus; Herpes simplex virus 1 and 2 (HSV-1 and HSV-2); *Histoplasma capsulatum*; *Ancylostoma duodenale* and *Necator americanus*; Human bocavirus (HBoV); *Ehrlichia ewingii*; *Anaplasma phagocytophilum*; Human metapneumovirus (hMPV); *Ehrlichia chaffeensis*; Human papillomavirus (HPV); Human parainfluenza viruses (HPIV); *Hymenolepis nana* and *Hymenolepis diminuta*; Epstein-Barr Virus (EBV); Orthomyxoviridae family; *Isospora belli*; Kingella kingae; Lassa virus; *Legionella pneumophila*; *Legionella pneumophila*; *Leishmania* genus; *Mycobacterium leprae* and *Mycobacterium lepromatosis*; *Leptospira* genus; *Listeria monocytogenes*; *Borrelia burgdorferi* and other *Borrelia* species; *Wuchereria bancrofti* and *Brugia malayi*; Lymphocytic choriomeningitis virus (LCMV); *Plasmodium* genus; Marburg virus; Measles virus; Middle East respiratory syndrome coronavirus; *Burkholderia pseudomallei*; *Neisseria meningitidis*; *Metagonimus yokagawai*; *Microsporidia phylum*; Molluscum contagiosum virus (MCV); Monkeypox virus; Mumps virus; *Rickettsia typhi*; *Mycoplasma pneumoniae*; (Actinomycetoma) and fungi (Eumycetoma); parasitic dipterous fly larvae; *Chlamydia trachomatis* and *Neisseria gonorrhoeae*; *Nocardia asteroides* and other *Nocardia* species; *Onchocerca volvulus*; *Paracoccidioides brasiliensis*; *Paragonimus westermani* and other *Paragonimus* species; *Pasteurella* genus; *Pediculus humanus* capitis; *Pediculus humanus* corporis; Phthirus pubis; *Bordetella pertussis*; *Yersinia pestis*; *Streptococcus pneumoniae*; *Pneumocystis jirovecii*; Poliovirus; *Prevotella* genus; *Naegleria fowleri*; JC virus; *Chlamydophila psittaci*; *Coxiella burnetii*; Rabies virus; Respiratory syncytial virus (RSV); *Rhinosporidium seeberi*; Rhinovirus; *Rickettsia* genus; *Rickettsia akari*; Rift Valley fever virus; *Rickettsia rickettsii*; Rotavirus; Rubella virus; *Salmonella* genus; SARS coronavirus; *Sarcoptes scabiei*; *Schistosoma* genus; *Shigella* genus; Varicella zoster virus (VZV); *Variola major* or *Variola minor*; *Sporothrix schenckii*; *Staphylococcus* genus; *Staphylococcus* genus; *Strongyloides stercoralis*; *Treponema pallidum*; *Taenia* genus; *Clostridium tetani*; *Trichophyton* genus; *Trichophyton tonsurans*; *Trichophyton* genus; *Epidermophyton floccosum*; *Trichophyton rubrum*; and *Trichophyton mentagrophytes*; *Trichophyton rubrum*; *Hortaea werneckii*; *Trichophyton* genus; *Trichophyton* genus; *Malassezia* genus; *Toxocara canis* or *Toxocara cati*; *Toxocara canis* or *Toxocara cati*; *Chlamydia trachomatis*; *Toxoplasma gondii*; *Trichinella spiralis*; *Trichomonas vaginalis*; *Trichuris trichiura*; *Mycobacterium tuberculosis*; *Francisella tularensis*; *Ureaplasma urealyticum*; *Coccidioides immitis* or *Coccidioides posadasii*; Venezuelan equine encephalitis virus; Guanarito virus; West Nile virus; *Trichosporon beigelii*; *Yersinia pseudotuberculosis*; *Yersinia enterocolitica*; Yellow fever virus; and Mucorales order (Mucormycosis) and Entomophthorales order (Entomophthoramycosis).

Second immunogens that are related to the tumor or infectious agent, may include isolated proteins, isolated portions of proteins (polypeptides), dendritic cell vaccines, antigen-pulsed dendritic vaccines, and dendritic cells pulsed with a cytomegalovirus (CMV) RNA such as integument protein pp65 RNA. Bacterial proteins or RNA may be used. Other viral RNAs or proteins may be used. Parasite or fungal proteins or RNA may be used.

Fusion protein may be used as a way to deliver either the first immunogen alone, or both the first and the second immunogen fused together. Fusion proteins are typically made using well known techniques in the art using recombinant DNA. Alternatively two or more proteins may be joined together by chemical means or enzymatic means, i.e., post-translationally. Fusion of a first immunogen with CCL3 may deliver a more potent stimulation than either of the two alone. The construction of fusion proteins is routine and well known in the art.

Combinations of agents may be combined together in a single composition or mixture or can be joined by fusion. Two agents can be administered simultaneously, approximately simultaneously, or serially. The first and second immunogens (or chemokine/cytokine and immunogen) may be administered separated by at least 12, 24, 36, or 48 hours. They may be administered within 48, 60, or 72 hours. If the two immunogens or agents are to be administered serially, they may advantageously be packaged together in a single container but in separate vessels. Such a container can be termed a kit and may additionally comprise instructions or other information, as well as additional agents or delivery means. Adjuvants may be added as separate elements of a kit or may be added to individual components in combination. Delivery devices may also be included in the kit, such as syringes and/or needles.

Any mammal can be treated in this manner, including but not limited to lab animals, such as rats, mice, guinea pigs, chimpanzees, monkeys. Humans can be treated. Domestic animals such as dogs and cats can be treated. Farm animals, whether for dairy production or meat production, such as cows, goats, pigs, and horses can be so treated. Zoo animals can be so treated.

Results from our trial appear to demonstrate that the modulation of CMV-specific DCs with Td pre-conditioning increases their migratory capacity and may improve clinical outcomes in patients with GBM. Corroborating studies in mice support these claims and underline CCL3 as a novel and important mediator of increased DC migration to VDLNs, in addition to its described roles in DC precursor mobilization to peripheral sites of inflammation[18,19] and in guiding naive CD8+ localization to sites of DC-CD4+ interactions in lymph nodes[20]. Our preclinical findings suggest that increased DC migration to VDLNs following Td pre-conditioning could be mediated through the induction of CCL21 and that CCL3 may be involved in enabling this step. However, it remains possible that additional mechanisms could also contribute to the increased DC accumulation in VDLNs. Evaluating efficacy in cancer vaccine trials is currently complex due to the lack of reliable immunologic predictors of clinical outcomes. However, our findings suggest that DC migration should be further investigated as a biomarker for immunotherapy studies.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Methods

Patient Selection, Demographics and Clinical Protocol.
The clinical protocol and informed consent were approved by the U.S. Food and Drug Administration and Institutional Review Board at Duke University. Adults with a newly-diagnosed WHO Grade IV GBM, who had a gross total resection and residual radiographic contrast enhancement on post-resection magnetic resonance imaging (MRI) not exceeding 1 cm in diameter in two perpendicular axial planes, and a Karnofsky Performance Scale score of ≥80, were eligible for the clinical study (FDA-IND-BB-12839, Duke IRB Pro00003877, NCT00639639). Histopathology of all specimens was initially read as GBM, but this diagnosis was re-confirmed by a second board-certified neuropathologist. Histologic diagnosis included immunohistochemistry for MGMT protein expression. Benign endothelial cells staining positive for MGMT served as the internal control[21]. MGMT promoter methylation was performed by PCR. Based on published reports showing high expression of CMV viral proteins in >90% of GBM tumors[9-12], we elected not to include pp65 staining of tumor tissue as an eligibility criterion for this trial. All 13 patients on study received a gross total resection defined as >90% with residual contrast enhancement of <1 cm$^2$, and steroid doses could not exceed 2 mg/day of dexamethasone. No patients received intensity-modulated radiation therapy (IMRT) or had 5-aminolevulinic acid (5-ALA) dye used during resection. Thereafter, all patients completed a six week course of conformal external beam radiotherapy (XRT) to a dose of 60 Gray (Gy) with concurrent temozolomide (TMZ) at a targeted daily dose of 75 mgm$^2$/d. Upon completion of standard therapy, all patients underwent an MRI for evidence of progressive disease. Those with evidence of progressive disease or required steroid therapy in excess of physiological levels at the time of vaccination were replaced. A total of 13 patients were enrolled and randomized prior to the first cycle of standard-of-care 5-day TMZ (200 mg/m$^2$/day), but one progressed before randomization. For each vaccine 2×10$^7$ mature pp65 RNA-pulsed DCs in 0.4 mL of saline were given intradermally in the groin. The first vaccination occurred on day 21±2 of TMZ cycle I. Although some patients (n=5) were also randomized to receive an autologous lymphocyte transfer, those patients did not show a significant improvement in progression-free survival or overall survival. Patients given autologous lymphocytes were additionally administered 3×10$^7$ cells/kg intravenously with acetaminophen (650 mg per os (po)) and Benadryl (25-50 mg po) given 30-60 minutes before infusion. The first three DC vaccines were given biweekly, and, at vaccine 4, patients were randomized to Td or unpulsed autologous DCs and received $^{111}$In-labeled DCs for migration studies. Vaccine 4 and additional monthly vaccines until tumor progression occurred on day 21±2 of successive TMZ cycles. A minimum of six cycles of adjuvant TMZ were required as per standard-of-care and continuation was at the discretion of the treating neuro-oncologist. Patients were monitored for treatment-related toxicity, and none of the patients experienced any vaccine or Td-related adverse events.

Human Autologous DC Generation for Vaccination and Production of Pp65-LAMP/A64 mRNA.

DCs were generated using the method of Romani et al.[22,23], and after harvest the cells were frozen and assessed for contamination and lineage purity as previously published[24]. The 1.932 kB pp65 full-length cDNA insert was obtained from Dr. Bill Britt (University of Alabama-Birmingham, Birmingham, Ala.) and RNA was generated and transfected as previously reported[23].

Human DC Migration Studies.

DC migration studies were done at the fourth vaccination. Patients were randomized by side to have one inguinal vaccination site pre-treated with either 1×10$^6$ unpulsed DCs or Td toxoid (1 flocculation unit (Lf)). Saline was administered on the contralateral side. Vaccination site pretreatment was done 6 to 24 hours before DC vaccination. DCs were labeled with 10 µCi/1×10$^7$ DC with $^{111}$In (GE Healthcare, Arlington Heights, Ill.) and divided equally in the two sites. Gamma camera images (GE Infinia Hawkeye) were taken immediately after injection and at 24 and 48 hours after injection to compare $^{111}$In-labeled DC migration from the inguinal injection sites to the inguinal lymph nodes.

Progression-Free and Overall Survival.

The more recent Response Evaluation Criteria in Solid Tumors (RECIST criteria) judge progression by measuring the longest one-dimensional diameter and determine progression by a 20% increase in this diameter[25]. Once progression is detected on MRI, other imaging modalities such as positron emission tomography and a stereotactic brain biopsy of the enhancing region are incorporated to aid in determining progression. A stereotactic brain biopsy or resection demonstrating recurrence defines clinical progression. Progression-free survival (PFS) was defined as the time until radiographic or clinical progression and was censored at the last follow-up if the patient remained alive without disease progression. Overall survival (OS) was defined as the time until death and was censored at the last follow-up if the patient remained alive at the time of analysis. PFS and OS for all patients were calculated from both the time of surgery and from randomization to vaccine site pre-conditioning.

Mice.

All animal experiments were performed according to Duke University Institutional Animal Care and Use Committee-approved protocols. Female C57BL/6 wild-type, OT-I transgenic mice, Ccl3$^{-/-}$, and RFP and GFP transgenic mice (ubiquitin promoter) were obtained from the Jackson Laboratory and were bred under pathogen-free conditions at Duke University Medical Center. The plt strain was provided by M.D.G, and maintained at Duke University Medical Center. All mice were bred under pathogen-free conditions at Duke University Medical Center.

Generation of Murine Bone Marrow-Derived DCs, Electroporation, and Phenotyping.

Bone marrow-derived DCs were generated from 6-8 week old female C57BL/6 wild-type, RFP$^+$, or GFP$^+$ transgenic mice and pulsed with OVA RNA as previously described[23]. For phenotyping, anti-mouse PE-conjugated CD11c (HL3), CD80 (16-10A1), CD86 (GL1), Ly-6G (1A8), MHC class II (I-A$^b$; AF6-120.1) and isotype controls (IgG1; G235-2356. IgG$_{2a}$, κ; R35-95) were from BD Pharmingen. Cells were washed, resuspended in PBS and 2% FBS, incubated at 4° C. for 30 minutes, and washed again before use.

Vaccine Site Pre-Conditioning and DC Vaccination in Mice.

For Td immunization, female 6-8 week old C57BL/6 mice received a primary i.m. vaccine of Td toxoid (Sanofi Aventis; DECAVAC®; 1Lf, 100 µL) administered bilaterally into the quadriceps muscle (50 uL per leg). An i.m. booster (0.5 Lf, 50 µL) was administered two weeks later. Vaccine site pre-conditioning with saline or Td toxoid (0.5 Lf) was given i.d. two weeks after the booster and randomized to the right or left groin site. Mouse IgG antibody responses to Td were measured by ELISA (Xpress Bio). Serum from immunized mice was harvested two weeks following each immunization prior to the next booster vaccine. DCs were resuspended at 1×10$^6$/100 µL PBS (Gibco) and administered i.d. on both sides 0.8 cm from the groin crease 24 hours after i.d. pre-conditioning. DCs injected in the groin ipsilateral to the Td pre-conditioning side were directly injected i.d. within the erythematous nodule produced by Td pre-conditioning.

For recall response experiments using other protein antigen formulations, female 6-8 week old C57BL/6 mice received a primary i.m. vaccine of PREVNAR 13® (Pfizer, Pneumococcal 13-valent conjugate vaccine, 1.32 µg, 100 µL) and PEDVAX HIB® (Merck, Haemophilus b conjugate vaccine, 1.5 µg, 100 µL) administered bilaterally into the quadriceps muscle (50 µL per leg). Vaccine site pre-conditioning with saline or the protein antigen (50 µL) was given i.d. two weeks later and randomized to the right or left groin site. DC vaccines were given 24 hours later, and migration to lymph nodes was assessed 48 hours later. As with Td pre-conditioning, DCs injected in the groin ipsilateral to the pre-conditioning side were directly injected i.d. within the erythematous nodule produced by those formulations. For comparisons of other pre-conditioning agents, female 6-8 week old C57BL/6 mice received a unilateral dose of unpulsed, mature DCs ($1 \times 10^6$ in 50 µL) or TNF-α (30 ng) administered i.d. at the groin site 24 hours prior to DC vaccination. Based on the previous work using these pre-conditioning regimens, DC migration to bilateral inguinal lymph nodes was assessed 24 hours later. For all other migration experiments, popliteal and inguinal LNs were harvested 48 hours post-DC vaccination and digested for flow cytometry. The percent of migrating DCs was enumerated by gating on fluorescent DCs in wild-type VDLNs. DCs from wild-type (GFP$^-$ and RFP$^-$) mice as negative controls before gating on fluorescent DCs within VDLNs to account for background autofluorescent cells that may have appeared in the GFP channel. A sample size (at least three per group) was based on empirical evidence from previously published reports as the size necessary for adequate statistical analysis of lymph nodes sampled[26].

Depletion, Adoptive Transfer, and CCL3 Reconstitution.

Female 6-8 week old C57BL/6 mice were initially depleted of cellular subsets once daily (200 µg/mouse intraperitoneally) for three days prior to the first Td i.m. immunization. Anti-mouse CD4 (GK1.5) and anti-CD8 (2.43) antibodies were purchased from American Type Culture Collection (ATCC, Manassas, Va.). Anti-mouse NK1.1 (PK136) and anti-CD19 (2D5) and control isotype depleting antibodies (IgG2a (2A3) and IgG2b (LTF-2)) were from BioXCell. Maintenance doses of depletion antibodies were administered at three-day intervals (200 µg intraperitoneally) until vaccine site pre-conditioning with Td two weeks later. For adoptive transfer experiments, Td-activated CD4$^+$ T cells (CD4$_{Act}$) were induced in donor female 6-8 week old C57BL/6 mice. Mice were primed (1 Lf, 100 µL) and boosted (0.5Lf, 50 µL) i.m. with Td two weeks apart. Three days after the i.d. Td pre-conditioning, donor inguinal lymph nodes, skin injection sites, and spleens were harvested and processed for negative isolation of CD4$^+$ T cells (Miltenyi Biotec). Complementary sites from naive mice were harvested simultaneously and processed for negative isolation of CD4$^+$ T cells (CD4$_{Naive}$). A final dose of $6 \times 10^6$ CD4$^+$ T cells were administered intravenously into recipient mice two days before i.d. vaccination with RFP$^+$ DCs. For CCL3 reconstitution in Ccl3−/− hosts, recombinant mouse CCL3 (R&D Systems) was administered intravenously into the tail vein (10 µg/mouse) 12 hours prior to vaccination with RFP$^+$ DCs. Ccl3−/− mice that were Td-immune were given recombinant CCL3 12 hours following Td pre-conditioning at the vaccine site.

Tumor Implantation Experiments.

For tumor implantation experiments, B16/F10-OVA cells were grown as previously published[27] and injected subcutaneously at a concentration of $2 \times 10^5$ cells in 200 µL of PBS in the flank of C57BL/6 mice 8 days before vaccine site pre-conditioning, the first intradermal vaccine of OVA RNA-pulsed DCs, and autologous lymphocyte transfer (1:1 infusion of naive: OT-I OVA-specific T cells). Randomization of mice occurred after tumor inoculation prior to vaccine site pre-conditioning and the first DC vaccine first by compilation and then by random sorting into various treatment cages. Mice received two additional weekly vaccines of RNA-pulsed DCs on days 15 and 22. Ten days after tumor implantation, flank sites were monitored daily for tumor growth, and tumor size was measured every two days. Tumor volume (millimeters cubed) was calculated by the formula (length×width$^2$×0.52) in a perpendicular fashion. Mice were sacrificed when ulceration occurred or when the tumor reached either 2 cm in any direction or 2000 mm$^3$. Analysis of tumor growth focused on follow-up assessments before significant dropout occurred. A logarithmic transformation yielded a linear relationship between tumor volume and time for all curves. A mixed effects linear model that accounted for correlation of measurements within a mouse was used to examine the relationship between time and log [tumor volume+1]. No blinding was done for these animal studies.

Mouse Tumor Cell Lines.

The B16/F10-OVA tumor cell line was a kind gift from R. Vile, PhD (Mayo Clinic)[27,28]. The B16/F10 cell line was provided by I. Fidler. PhD (M. D. Anderson Cancer Center, Houston, Tex.)[29]. Cell lines were tested for *mycoplasma* before use.

Murine Lymph Node Digestion and Quantification of Fluorescent and Endogenous DCs.

Harvested LNs were placed in 6-well culture plates containing 1 mL HBSS with Ca$^{2+}$/Mg$^{2+}$ (Gibco), digested for 35 min at 37° C. with collagenase A (1 mg/mL; Roche) and DNaseI (0.2 mg/mL; Sigma-Aldrich) and 20 mM EDTA (Invitrogen) was added for 5 minutes at room temperature to stop the reaction[26]. Single cell suspensions were prepared, cells were centrifuged (500×g×5 min) and resuspended in PBS with 2% FBS and stained with murine APC-conjugated CD11c (BD Pharmingen; HL3). For quantification of RFP$^+$ or GFP$^+$ counts in individual lymph nodes, samples were resuspended at an equal volume and 50 µL of counting beads (Invitrogen; 50,000 beads) were added to each sample. Cells were gated first on murine CD11c$^+$ cells and then RFP$^+$ or GFP$^+$ cells, and absolute cell counts/lymph node were quantified using the following equation: RFP$^+$ or GFP$^+$ events×50,000 beads/# bead events. For endogenous DC migration experiments, cells were surface-stained in PBS with 3% FBS, 10 mM EDTA, 5% normal mouse serum, 5% normal rat serum and 1% Fc Block (eBioscience; clone 93) and then intra-cellularly stained with anti-CD207 according to the manufacture's protocol (BD CYTOFIX/CYTOPERM™ fixation and premabilizationKit). The cells were analyzed by BD LSRII flow cytometer with FLOWJO® software (Tree Star). FITC-conjugated anti-B220 (RA-3-6B2), ALEXA FLUOR® 700 (mouse anti-human CD3)-conjugated anti-Ly-6G (1A8), APC-Cy7-conjugated anti-CD11b (M1/70), V450-conjugated anti-Ly-6C (AL-21) are from BD Pharmingen. PE-conjugated anti-CD207 (eBioL31), PE-Cy5.5-conjugated anti-CD11c (N418), PE-Cy7-conjugated anti-CD8 (53.6.7), APC-conjugated anti-CD103 (2E7), EFLUOR® (organic dye) 605NC-conjugated anti-CD45 (30-F11) and EFLUOR® (organic dye) 650NC-conjugated anti-MHC Class II (I-A/I-E) (M5/114.15.2) are from eBioscience. FITC-conjugated anti-CD3 (145-2C11) and anti-CD49b (DX5) are from BioLegend. LIVE/DEAD® Fixable Aqua Dead Cell Stain Kit is from Molecular Probes.

Serum Cytokine and Chemokine Analysis.

Peripheral blood was collected 24 hours after vaccine site pre-conditioning prior to DC vaccination. For patients, blood was collected in 10 mL venous collection tubes (BD), allowed to clot, spun at 1,170×g for 15 minutes, and serum was stored at −190° C. For mice, blood was collected in microtainer tubes (BD) allowed to clot for 30 min, spun at 8,000×g for 5 min, and serum was stored at −80° C. Multiplex cytokine and chemokine kits were used for patient and mouse studies (cytokines and chemokines of interest for human, Affymetrix and Millipore: EPX080-10007-901, EPX010-12121-901, EPX010-12125-9, EPX010-10287-901, HCYTOMAG-60K-01 MDC; for mouse: Affymetrix and Millipore: EPX090-20821-901 PROCARTAPLEX™ 9 plex, MCYP3MAG-74K-01 MDC) following the manufacturer's instructions.

Expression of Chemokines CCL3 and CCL21 in Mice.

Female 6-8 week old C57BL/6 or Ccl3−/− mice were immunized with Td as described above. Twenty-four hours following Td pre-conditioning, both left and right skin sites and inguinal lymph nodes were harvested. For protein isolation, skin and lymph node samples were placed in pre-loaded bead lysis EPPENDORF TUBES™ (tubes)(Next Advance) containing RIPA buffer (Sigma) with protease inhibitor cocktail tablets (Mini Complete Protease Inhibitor Cocktail Tablets, Roche Applied Science). Homogenization was performed with the Bullet Blender at 4° C. Supernatants were collected by centrifugation, and chemokines were quantified by ELISA. QUANTIKINE® kits (R&D Systems) were used for CCL3, and RayBiotech ELISA kits were used for CCL21. Corresponding samples were run for total protein concentration using the Bradford assay. CCL3 and CCL21 concentrations were normalized across samples and expressed as pg per mg or ng per mg of total skin or lymph node protein.

Statistical Analysis.

Statistics were reviewed by biostatisticians and tested as described in results and figure legends. Cox proportional hazard models were used to evaluate DC migration and clinical outcomes. The Logrank test was used to compare Kaplan-Meier survival curves with censored patient data. An unpaired two-sample student's t test was used for two-group comparisons. Paired t tests were used for comparisons between lymph nodes in the same host. One-way ANOVA was used to assess differences among three or more groups with post-hoc Tukey t tests for two-group comparisons. Wilcoxon rank sum analyses were conducted for pairwise comparisons in serum cytokine/chemokine panels. Signed rank tests were used to evaluate fold increase in chemokine levels. For tumor growth curves, a mixed effects linear model was employed utilizing log-transformed curves and F-test for pairwise comparisons of regression line slopes and mean tumor volumes on the first day of detectable tumors (y-intercept). Repeated measures for calculation of slopes incorporated time between detectable tumor until significant dropout occurred (maximal tumor size, ulceration, or death). Mean tumor volumes at final time points when entire control cohort expired were compared between two groups using an unpaired two-sample student's t test. Asterisks indicate level of significance (*$P<0.05$, $P\leq0.01$, *$P<0.001$, $P>0.05$ not significant (N.S.)).

Example 2

To evaluate the influence of vaccine site pre-conditioning on DC migration clinically, we conducted a randomized and blinded clinical trial of patients with newly-diagnosed GBM (Extended Data FIG. 1). Thirteen patients consented to this trial but only 12 were randomized as one progressed prior to randomization (Extended Data Table 1). Patients were randomized to unilateral vaccine site pre-conditioning with unpulsed, autologous DCs[8] or Td, based upon its safety profile as a clinically-approved vaccine and our hypothesis that it would induce inflammation at the vaccine site[13]. The accumulation of injected DCs in vaccine site-draining lymph nodes (VDLNs) was significantly greater in patients given Td (FIG. 1a). Moreover, Td-treated patients also showed a significant increase in both PFS (FIG. 1b) and OS (FIG. 1c) from the time of randomization compared to DC-treated patients. From the time of diagnosis, patients receiving Td had a median PFS exceeding 36.6 months vs. 10.8 months for the DC cohort and a median OS exceeding 36.6 months vs. 18.5 months for the DC cohort. Thus, the median PFS and OS for the DC cohort were consistent with patients treated with the standard of care[14]. However, we cannot exclude that DC pre-conditioning actually had a negative effect on their observed PFS and OS for this cohort of patients with some favorable prognostic factors. Three censored patients from the Td cohort did not progress and were alive at the time of survival analysis (>36.6 months). Overall, these prognostic factors varied across both treatment groups as expected in a small clinical trial. However, there was no discernible trend across prognostic factors that would suggest these factors alone account for the observed differences in survival between cohorts. Using the both Curran et al. recursive partition analysis[15] and the European Organization for Research and Treatment of Cancer (EORTC) nomogram[16] for predicting outcome of patients with GBM, Td-treated patients exceed expected survival times by a far greater degree than do the DC-treated patients in both cases by nearly the same amount (Extended Data Table 1). The vaccine responses in long-term survivors varied in durability, but pp65-specific immune responses were detectable for several months in all long-term survivors. An increase in pp65-specific interferon-γ spot-forming units (SFUs) from baseline did correlate with overall survival and the two long-term survivors for which samples were available had the highest increases in pp65-specific immune responses after vaccination although the sample size is small. In addition, we observed a striking association between DC migration to the VDLNs and PFS (FIG. 1d) and OS (FIG. 1e) in patients with GBM receiving pp65 RNA-pulsed DC vaccines.

Example 3

Figures 2A, 2B, 2C, 2D:
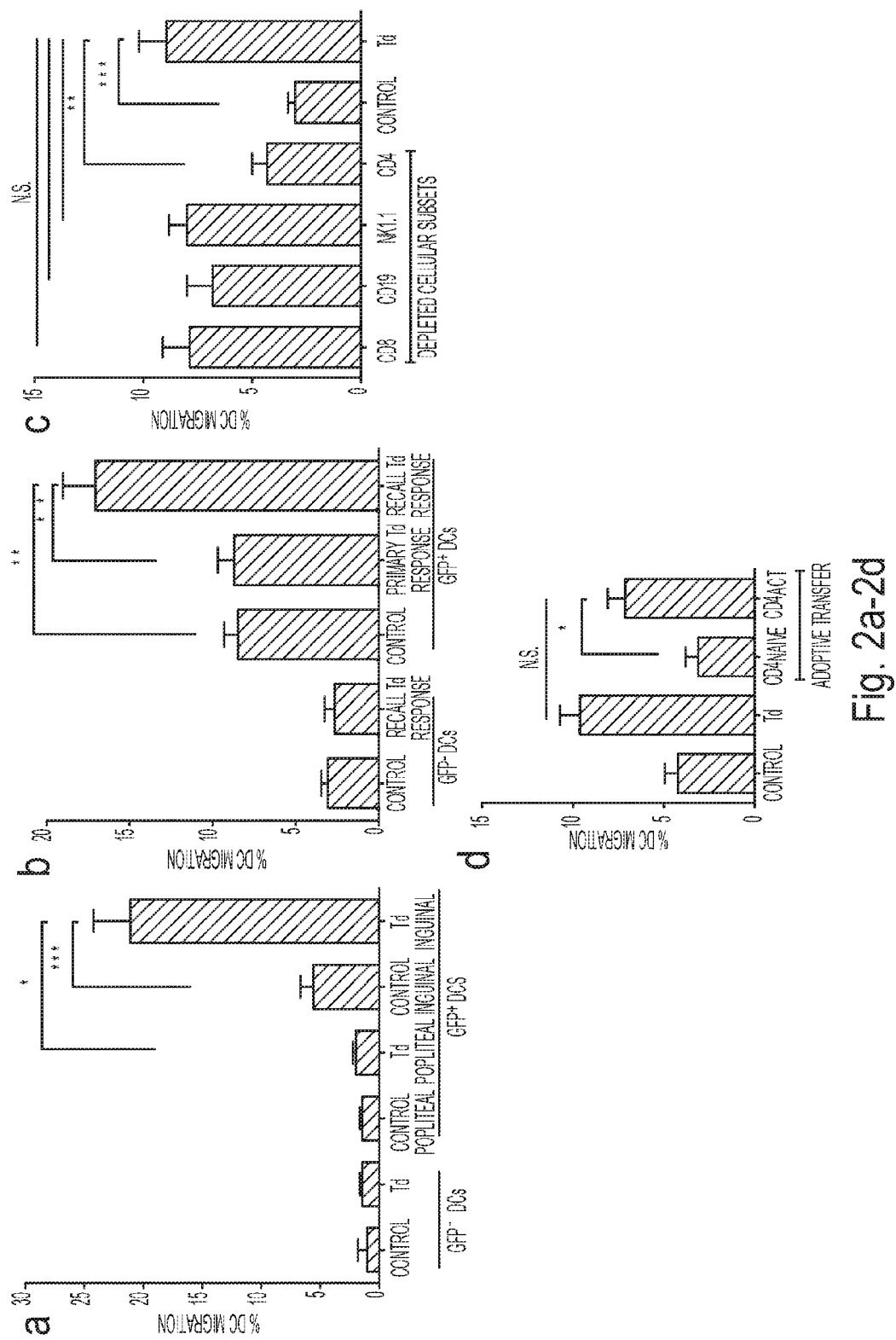
FIG. 2a-2f. Td recall response activates CD4$^+$ T cells to systemically increase DC migration to VDLNs.

To validate these clinical results and understand the mechanistic underpinnings, we performed analogous studies in a mouse model. Vaccine sites of Td-immune mice were pre-conditioned with Td and then received a bilateral vaccine of ovalbumin (OVA) RNA-pulsed DCs. In a striking parallel to our clinical findings, Td-immune mice receiving Td pre-conditioning had a three-fold increase in DCs within the afferent inguinal lymph nodes (FIG. 2a). This effect was attributable to Td-specific recall responses as mice not primed with Td (Td-naïve mice) did not display any increased DC migration to VDLNs (FIG. 2b). Vaccination and pre-conditioning with other CD4-dependent protein antigens also increased DC migration suggesting this may be a generalizable phenomenon (Extended Data FIG. 2). Subsequent studies performed in Td-treated mice demonstrated that only selective depletion of CD4+ T cells abrogated the increase in DC migration (FIG. 2c). The effect of enhanced migration was also transferable to naïve mice administered Td-activated CD4+ T cells (FIG. 2d).

Example 4

Figures 2E, 2F:
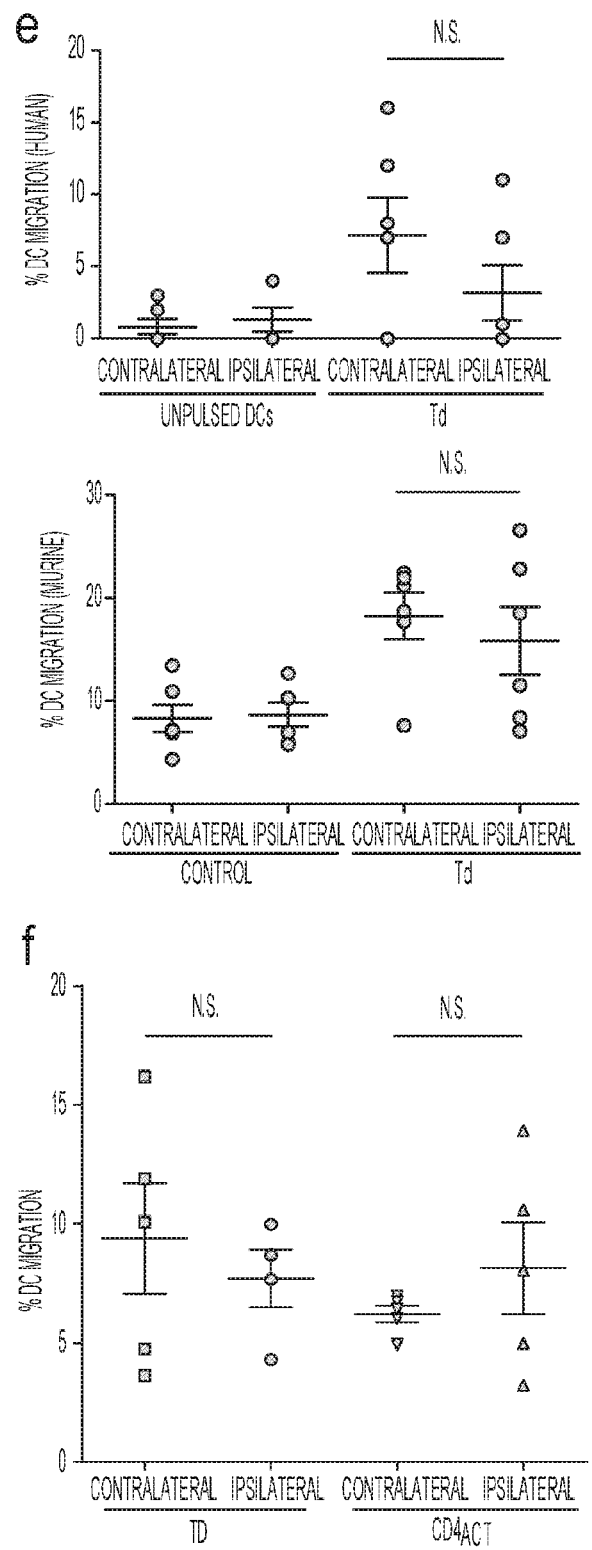

In patients with GBM randomized to unilateral Td pre-conditioning we observed an increased uptake of $^{111}$In-labeled DCs in bilateral lymph nodes, suggesting that Td pre-conditioning increased DC migration through systemic mediators (FIG. 2e, top). Parallel murine studies also demonstrated an increased uptake of DCs in the VDLNs contralateral and ipsilateral to the site of Td pre-conditioning (FIG. 2e, bottom). Subsequent experiments revealed that Td-activated CD4+ T cells administered systemically in naive mice were also sufficient to increase bilateral DC migration (FIG. 2f). We also directly compared Td to unpulsed DCs or TNF-α[8] but found they only increased DC migration ipsilaterally (Extended Data FIGS. 3a and 3b).

Example 5

Based on our observations that Td recall responses could induce bilateral DC migration and that systemic administration of Td-activated CD4+ T cells were sufficient to recapitulate the increased DC migration, we sought to examine the induction of CD4-dependent inflammatory mediators in the serum of patients and mice following a recall response with Td pre-conditioning. CCL3 was the only chemokine to be elevated in both patients and mice and had the greatest fold elevation of all chemokines in the serum of both following Td pre-conditioning (FIG. 3a) (Extended Data FIG. 4a-d).

Example 6

Figures 3A, 3B, 3C, 3D, 3E, 3F, 3G:
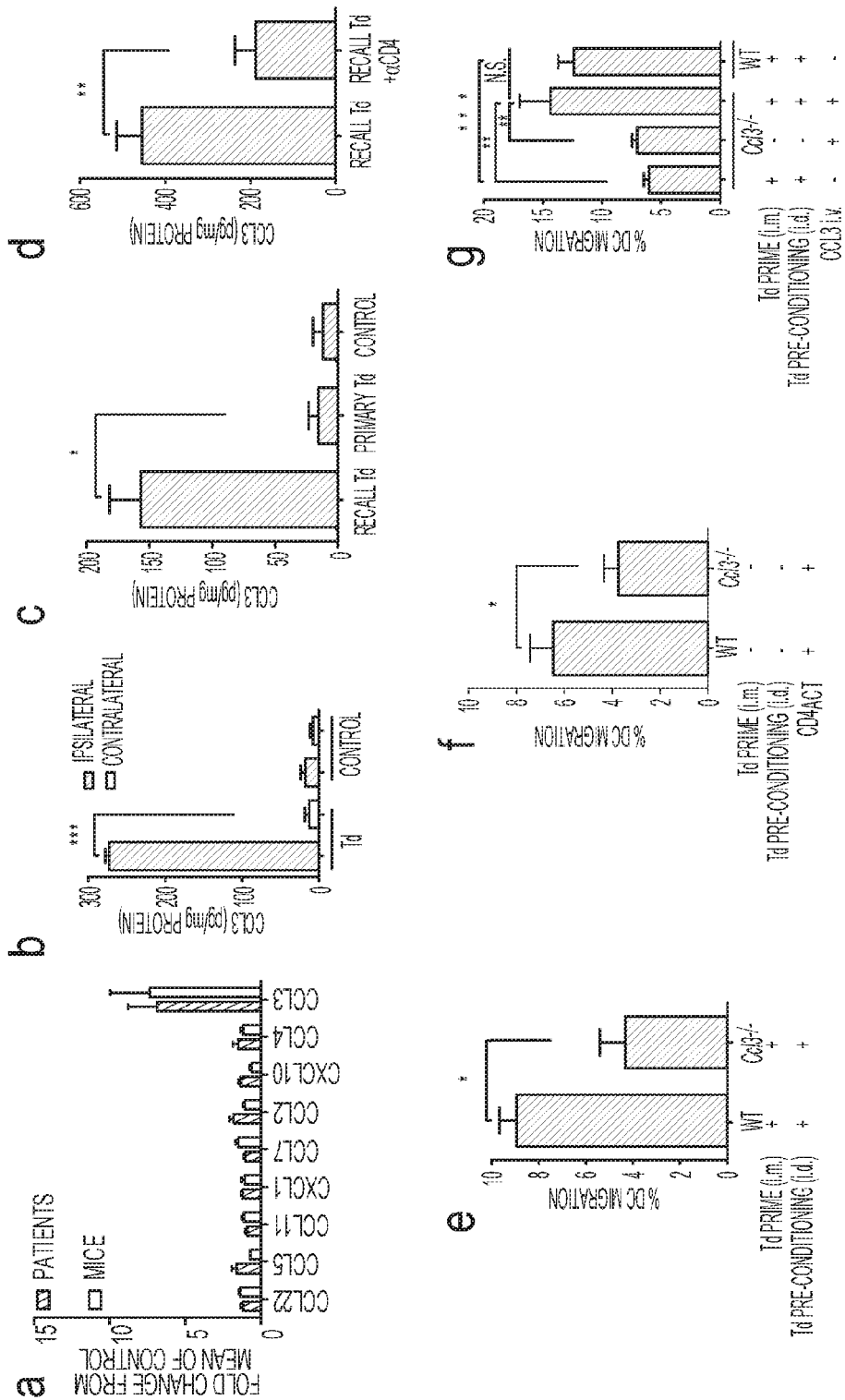
FIG. 3a-3j. Td recall and CCL3 induction at pre-conditioning site cooperate to provide CCL21-induced gradient to VDLNs.
Figure 5:
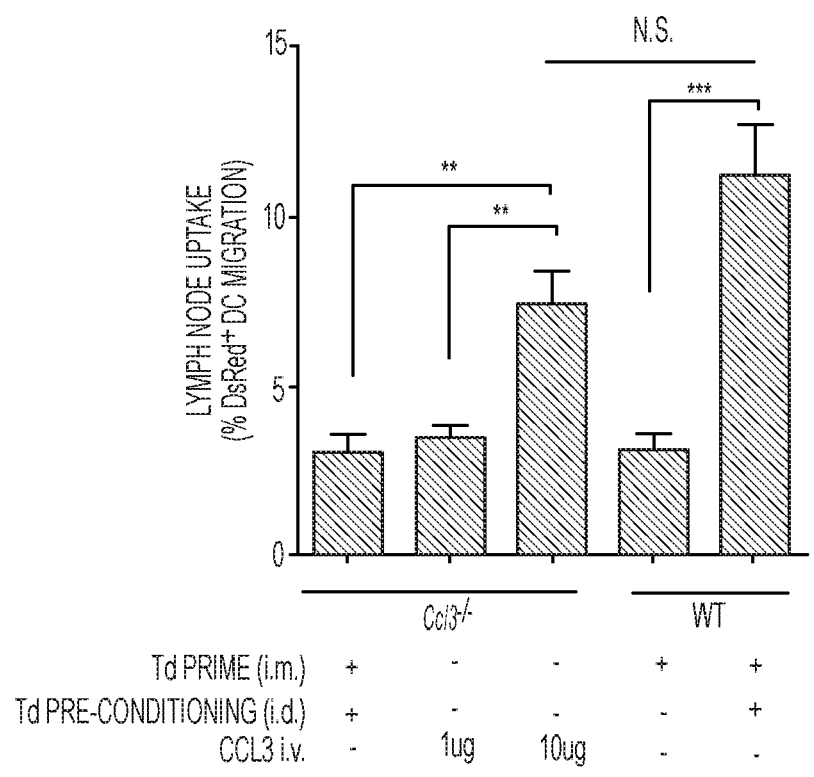
FIG. 5. Dose-dependent response of CCL3-mediated increased DC migration in Ccl3−/− hosts. Increasing doses of CCL3 alone without accompanying Td recall responses in Ccl3−/− hosts can rescue limited DC migration to draining lymph nodes. Asterisks indicate level of significance (*P<0.05, P≤0.01, *P<0.001, P>0.05 not significant (N.S.)).

To identify the site of the CCL3 production, we assayed the pre-conditioning sites in mice and found high concentrations of this chemokine only unilaterally at the site of Td pre-conditioning (FIG. 3b). Subsequent experiments showed that CCL3 upregulation in the skin was dependent on the induction of the Td recall response (FIG. 3c) and was significantly reduced by CD4+ T cell depletion (FIG. 3d). Time course experiments following DC vaccination revealed that the induction of CCL3 by Td pre-conditioning remained elevated over time compared to mice lacking Td recall responses (Extended Data FIG. 5).

Example 7

Figure 6:
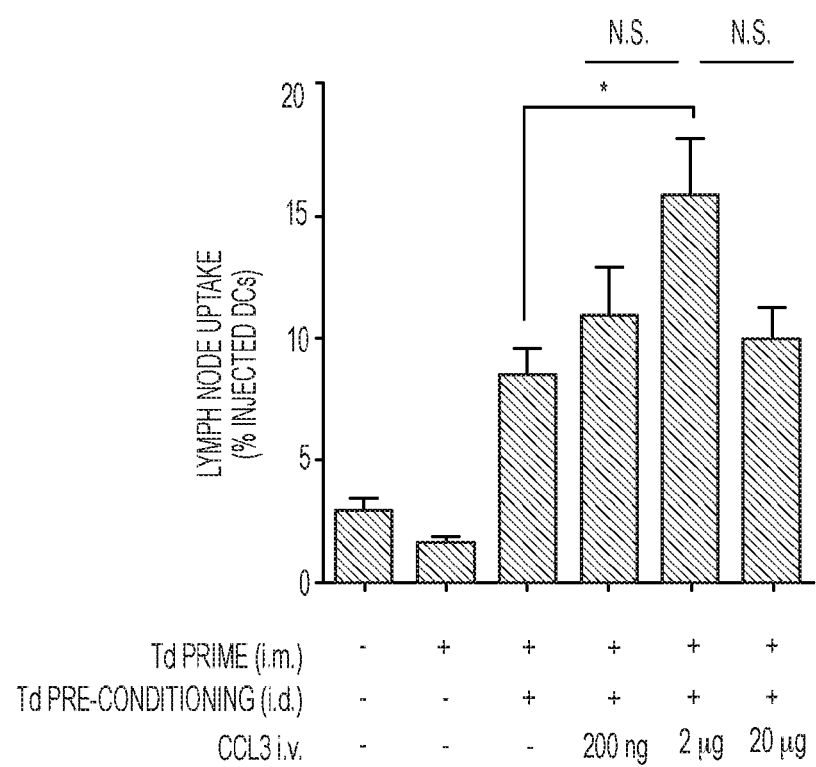
FIG. 6. Dose-dependent response of CCL3-mediated increased DC migration to draining lymph nodes in wild-type hosts. Dose response kinetics of CCL3 pre-conditioning in naive wild-type C57BL/6 hosts. DC migration is increased with CCL3 pre-conditioning compared to Td-treated mice at optimal doses prior to saturation with CCL3 protein. Asterisks indicate level of significance (*P<0.05, P≤0.01, *P<0.001, P>0.05 not significant (N.S.)).
Figure 7:
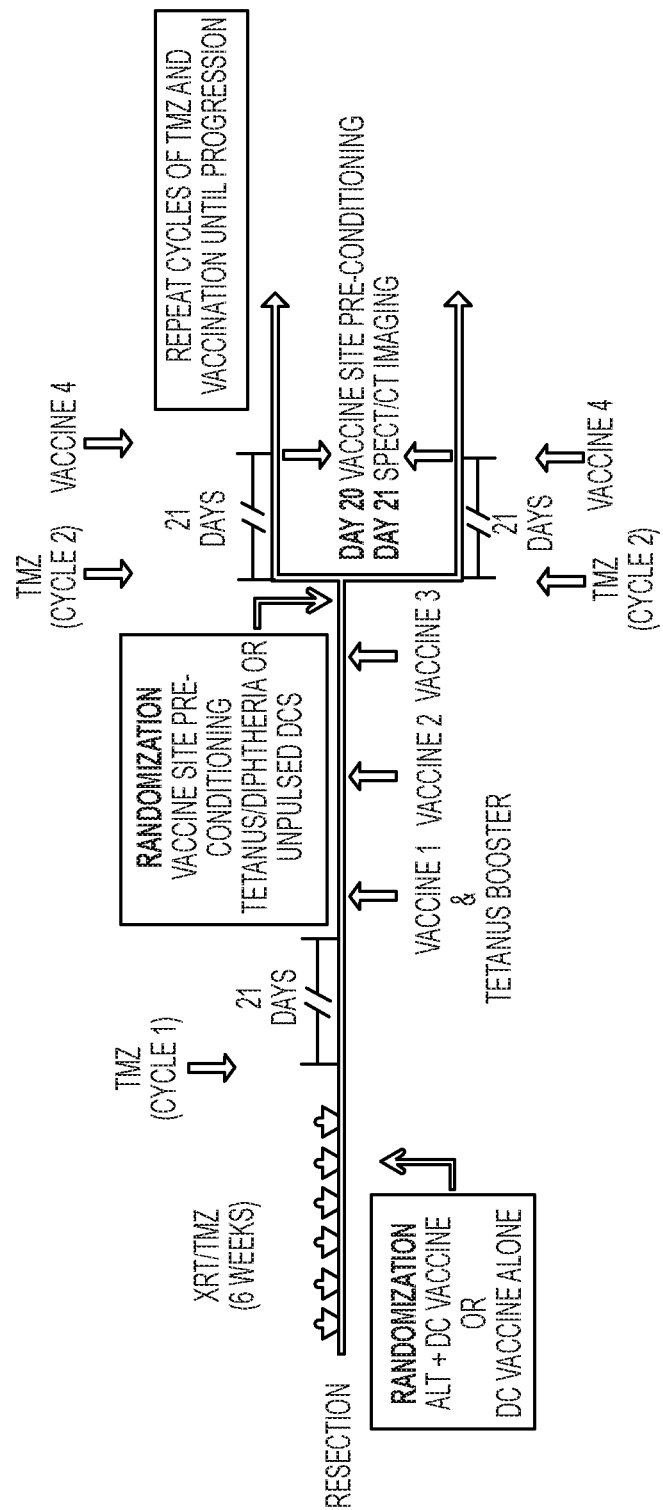
FIG. 7 (Extended Data FIG. 1). Schema of clinical trial.
Figure 8:
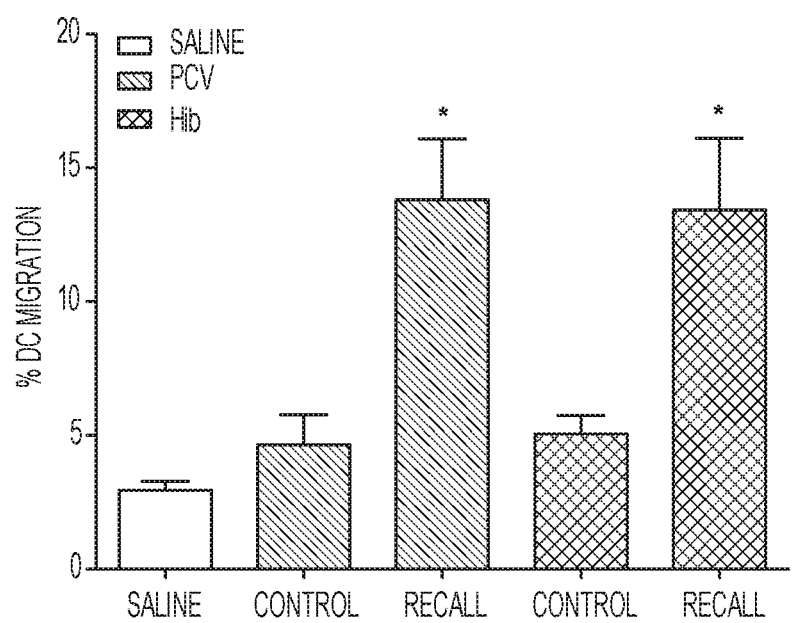
FIG. 8 (Extended Data FIG. 2). Recall responses induced by other CD4$^+$ T cell-dependent protein antigens increase DC migration to VDLNs. Primary immunization and vaccine site pre-conditioning with CD4$^+$ T cell-dependent protein antigens increase DC migration to VDLNs. Mice were immunized with either Haemophilus b conjugate (Hib) or pneumococcal 13-valent conjugate (PCV) intramuscularly and two weeks later received vaccine site pre-conditioning with the recall antigen or saline (Control). A separate cohort of mice were given saline only throughout the immunization schedule (Saline) (n=4 per group). Percent migration of RFP+DCs to VDLNs (***P<0.0001, one-way ANOVA; PCV Control vs. Recall, *P<0.05, Hib Control vs. Recall, *P<0.05, post-hoc Tukey t test). Representative of three experiments.
Figures 9A, 9B:
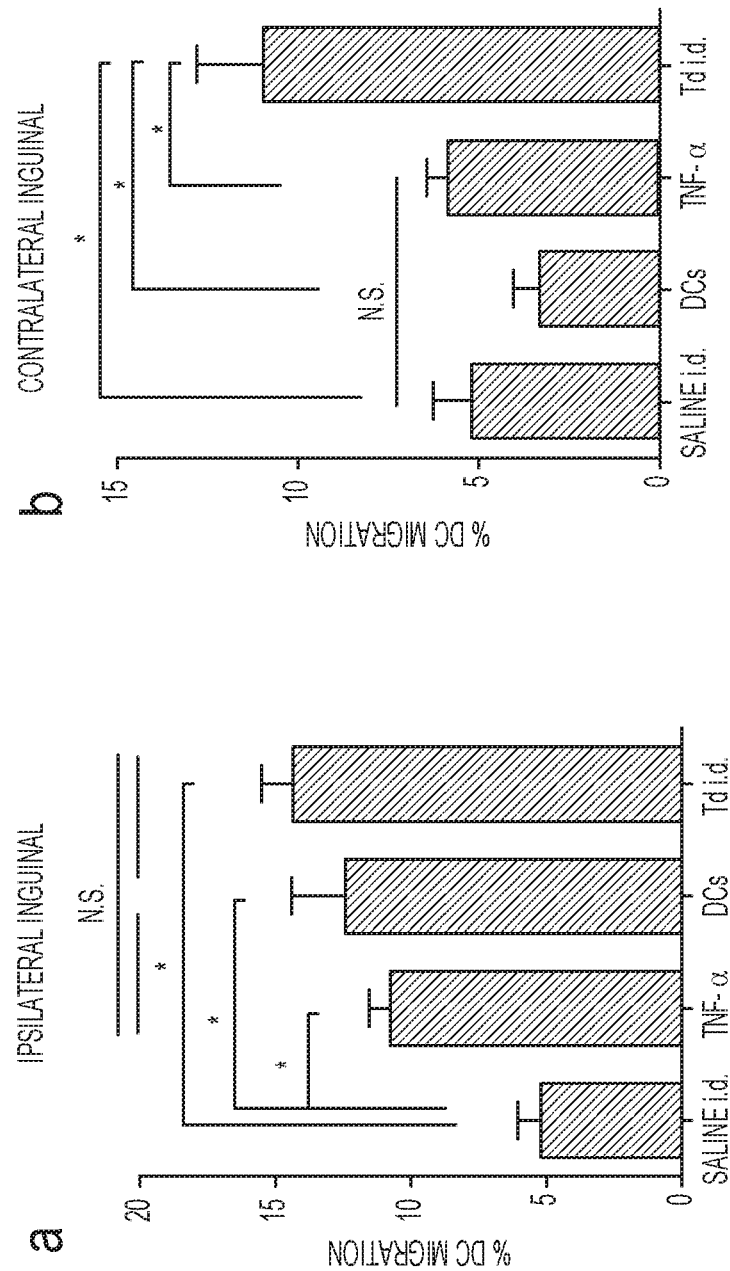
FIG. 9a-9b (Extended Data FIG. 3). Unilateral pre-conditioning with unpulsed DCs or TNF-α results in increased DC homing to ipsilateral draining inguinal lymph nodes. Mice were primed and pre-conditioned with Td or saline prior to administration of an OVA RNA-pulsed DC vaccine as described previously. Separate cohorts of naive mice received either 1×10$^6$ unpulsed DCs or 30 ng TNF-α on one side of the groin 24 hours prior to the bilateral RFP$^+$ DC vaccine. DC migration was quantified 24 hours post-vaccination.
Figures 10A, 10B, 10C, 10D:
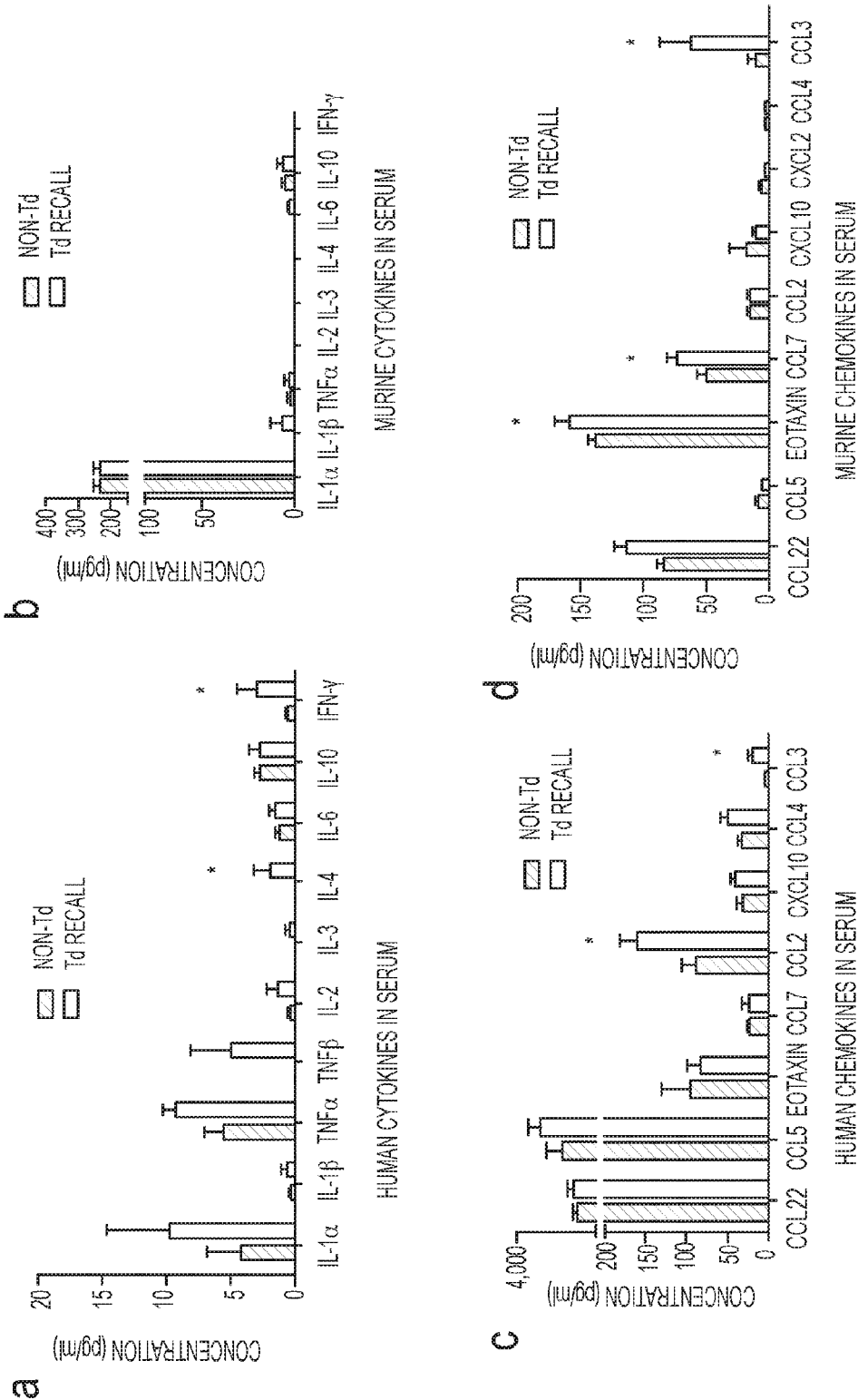
FIG. 10a-10d. (Extended Data FIG. 4.) Serum Cytokine and Chemokine Profile Following Td Pre-Conditioning in Patients and Mice.
Figure 11:
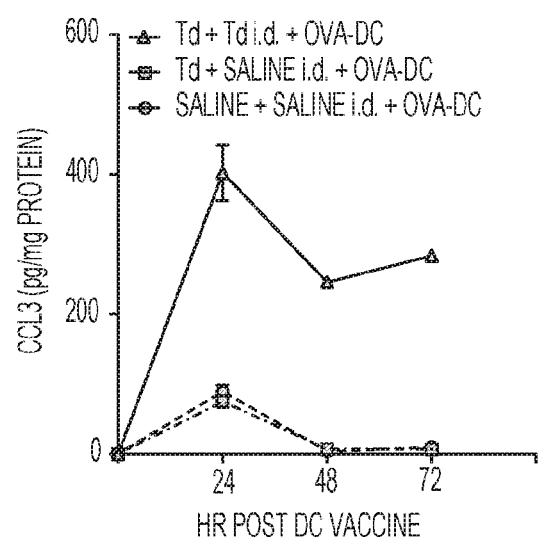
FIG. 11 (Extended Data FIG. 5). Vaccine site pre-conditioning results in CCL3 upregulation in Td-immune hosts. CCL3 remains elevated in the Td pre-conditioning site in the skin following DC vaccination (24, 48, and 72 hr, ***P=0.0001, Td+Td i.d.+OVA-DC vs. Td+saline i.d.+OVA-DC and Saline+saline i.d.+OVA-DC, *P<0.05, post-hoc Tukey t test). Representative of three experiments (n=4 per group).
Figures 12A, 12B:
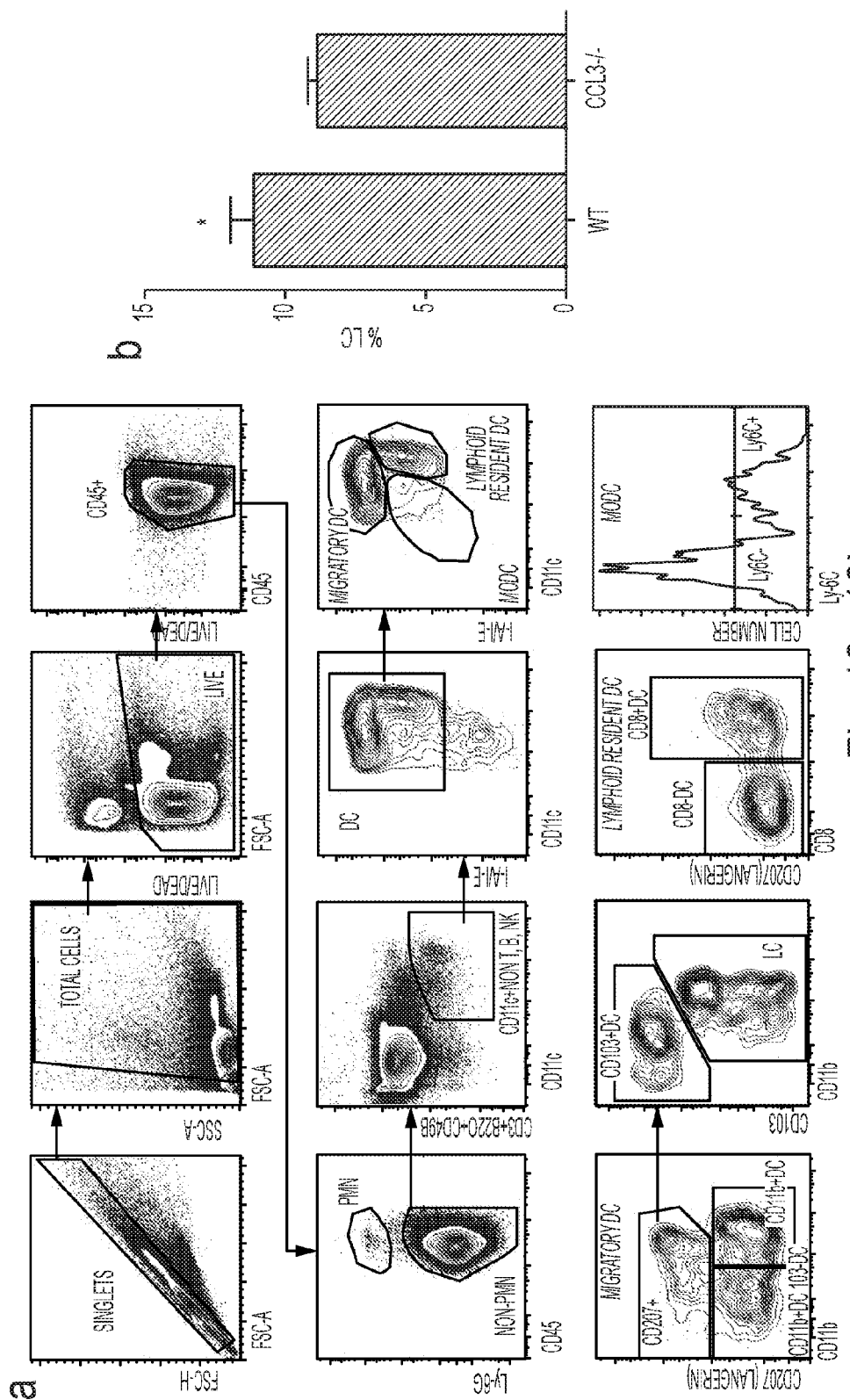
FIG. 12a-12b (Extended Data FIG. 6). Migratory DC subsets in wild-type and Ccl3−/− mice following induction of Td recall responses. Both wild-type and Ccl3−/− mice were first immunized with Td and then challenged with Td pre-conditioning. Migration of endogenous DC subsets to inguinal lymph nodes was assessed at day 4 and day 8 following pre-conditioning.
Figure 13:
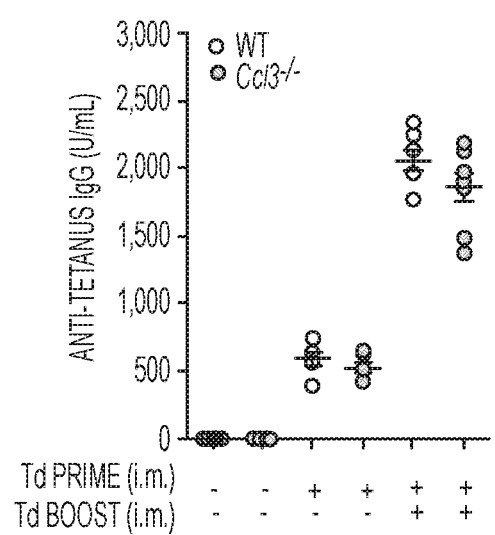
FIG. 13 (Extended Data FIG. 7). Anti-tetanus memory responses are induced and maintained in wild-type and Ccl3−/− mice throughout Td priming and boosting. WT and CCL3−/− mice primed and boosted with Td. Serum from immunized mice was harvested two weeks following each immunization prior to the next booster vaccine (P=0.28, P=0.14 paired two-sample t test following Td priming and boosting, respectively); Intramuscular (i.m.). Representative of three experiments (n=8 per group).

To evaluate the importance of CCL3 in mediating DC trafficking to VDLNs in vivo, we immunized and boosted Ccl3$^{-/-}$ mice with Td as described above and found that the migration of injected DCs to VDLNs in Ccl3$^{-/-}$ mice was significantly lower than in wild-type Td pre-conditioned mice (FIG. 3e). Similar experiments assessing the migration of endogenous DC populations revealed that resident Langerhans cells did not migrate as efficiently in Ccl3$^{-/-}$ hosts following Td pre-conditioning (Extended Data FIG. 6). To address the possibility that Td priming may have failed in Ccl3$^{-/-}$ mice due to some earlier role of CCL3, we compared the CD4 T-dependent immune responses to Td in both wild-type and Ccl3$^{-/-}$ hosts and found no differences in the ability of these two strains to mount anti-tetanus immune responses following Td priming and boosting (Extended Data FIG. 7).

Example 8

Our studies demonstrated that CD4+ T cells activated by the Td recall response were sufficient to induce increased DC migration in naive mice (FIG. 2d). To determine if Td-activated CD4+ T cells could reproduce this effect in Ccl3$^{-/-}$ hosts, we adoptively transferred these cells into Td-primed and pre-conditioned Ccl3$^{-/-}$ mice and assessed the migration of injected DCs. We found that they could not rescue the limited DC migration in Ccl3$^{-/-}$ hosts indicating that active CD4 T-cells were necessary, but not sufficient to increase DC migration (FIG. 3f). Exogenous administration of CCL3 could rescue the limited DC migration in Ccl3$^{-/-}$ mice, but only when the Td recall responses were induced (FIG. 3g), indicating that the ability of Td pre-conditioning to increase DC migration to VDLNs was dependent on both CD4+ recall responses and host-derived CCL3.

Example 9

Figures 3H, 3I, 3J:
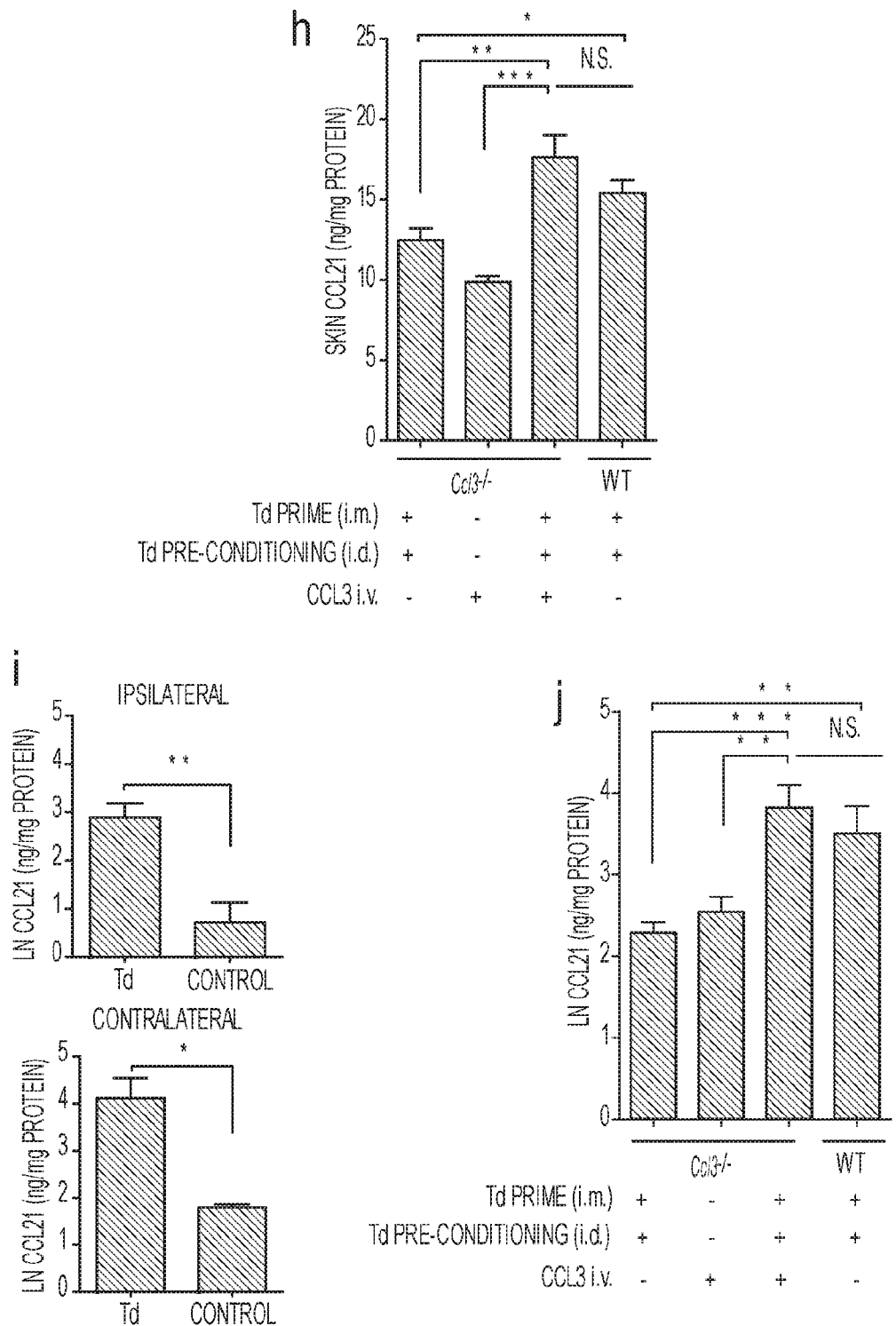

Alterations in CCL21 expression along the lymphatic endothelium in the skin take place in the context of inflammation and have been associated with increased DC migration[8]. Following Td pre-conditioning, higher levels of CCL21 were seen in Td-treated wild-type mice compared to Ccl3−/− mice, and exogenous administration of CCL3 rescued the diminished levels of CCL21 at the vaccine sites of Ccl3−/− mice only in the context of Td recall responses (FIG. 3h). Therefore, the ability of Td pre-conditioning to induce CCL21 levels at the vaccine site was dependent on both CD4+ recall responses and host-derived CCL3. Furthermore, Td pre-conditioning resulted in an increase in CCL21 in inguinal lymph nodes both ipsilateral and contralateral to the side of Td pre-conditioning (FIG. 3i). CCL21 expression in the VDLNs of Td-treated Ccl3−/− mice was expressed at levels lower than that of wild-type Td pre-conditioned mice. However, reconstitution of CCL3 back into Ccl3−/− mice significantly increased the expression of CCL21 in VDLNs, but only in the context of competent Td recall responses (FIG. 3j).

Example 10

Figures 4A, 4B, 4C, 4D:
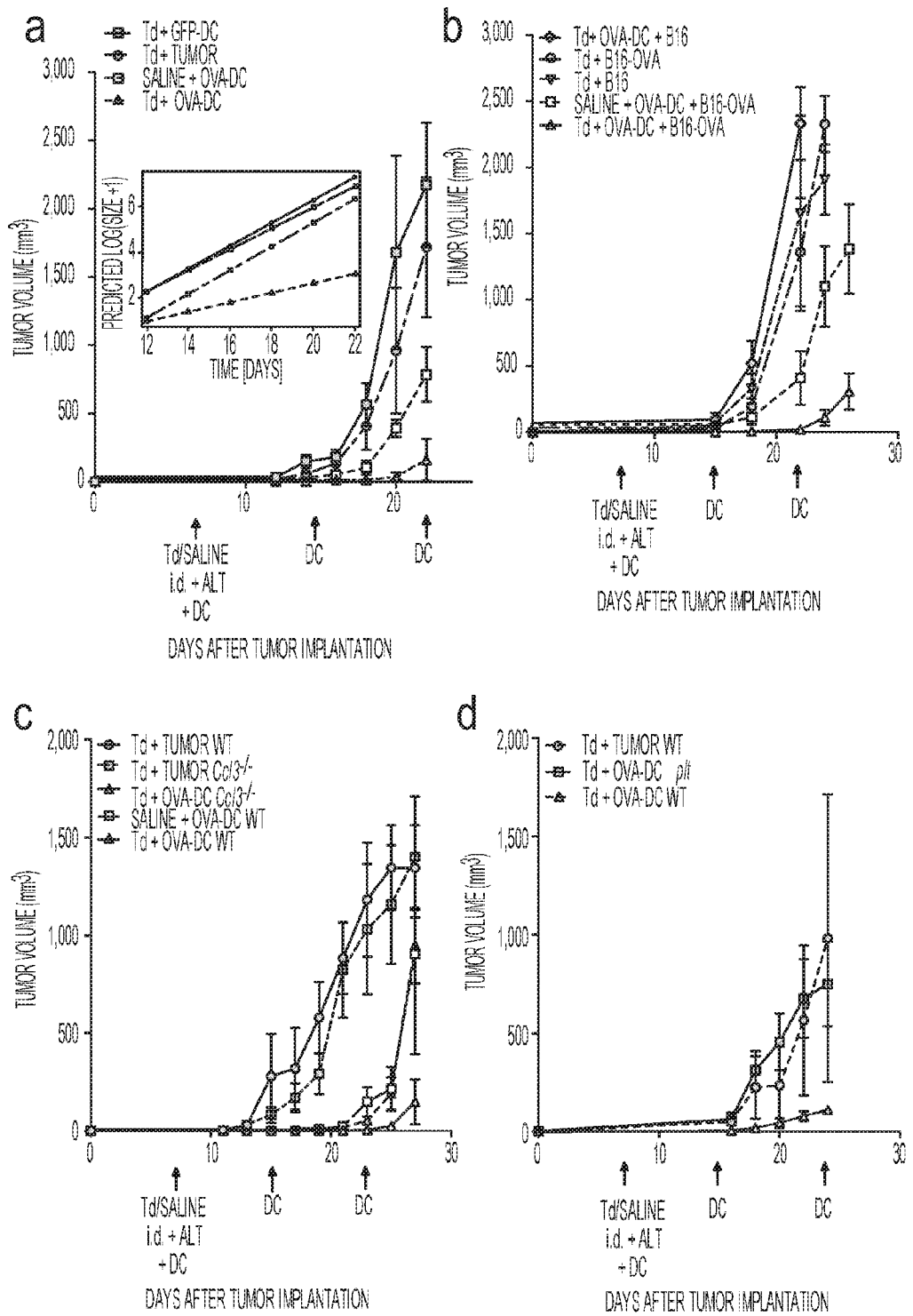
FIG. 4a-4d. Improved antitumor immunity in Td-treated mice is reliant on antigen specificity and functional CCL3-CCL21 axis.

The apparent increase in PFS and OS for Td treated-patients prompted us to determine if Td pre-conditioning could inhibit tumor growth in a murine model of established B16/F10-OVA tumors. Pairwise comparisons revealed that tumor growth in Td+OVA-DC mice was significantly delayed (FIG. 4a) in an antigen-dependent manner (FIG. 4b). Because host-derived CCL3 was found to be necessary for increased migration, as predicted, Td pretreatment in Ccl3$^{-/-}$ mice was unable to inhibit tumor growth (FIG. 4c). Similarly, plt (paucity of lymph node T cell) mice that lack expression of CCL21 in the lymph nodes[17], also failed to suppress tumor growth (FIG. 4d), indicating that Td-enhancement of OVA-DC vaccines was also reliant on the migratory pathway of the CCR7-CCL21 axis.

Example 11—Experimental Design

Vaccine Site Pre-Conditioning and DC Vaccination in Mice

For Td immunization, female 6-8 week old C57BL/6 mice received a primary i.m. vaccine of Td toxoid (Sanofi Aventis; DECAVAC®; 1Lf, 100 μL) administered bilaterally into the quadriceps muscle (50 uL per leg). An i.m. booster (0.5 Lf, 50 μL) was administered two weeks later. Vaccine site pre-conditioning with saline or Td toxoid (0.5 Lf) was given i.d. two weeks after the booster and randomized to the right or left groin site. Mouse IgG antibody responses to Td were measured by ELISA (Xpress Bio). Serum from immunized mice was harvested two weeks following each immunization prior to the next booster vaccine. DCs were resuspended at 1×106/100 µL PBS (Gibco) and administered i.d. on both sides 0.8 cm from the groin crease 24 hours after i.d. pre-conditioning. DCs injected in the groin ipsilateral to the Td pre-conditioning side were directly injected i.d. within the erythematous nodule produced by Td pre-conditioning.

Depletion, Adoptive Transfer, and CCL3 Reconstitution.

For CCL3 reconstitution in Ccl3−/− hosts, recombinant mouse CCL3 (R&D Systems) was administered intravenously into the tail vein (10 µg/mouse) 12 hours prior to vaccination with RFP+ DCs. Ccl3−/− mice that were Td-immune were given recombinant CCL3 12 hours following Td pre-conditioning at the vaccine site. In follow-up experiments assessing the dose-dependent response of CCL3 in Ccl3−/− hosts, 1 µg/mouse and 10 µg/mouse were administered intravenously 12 hours prior to the DC vaccine. In follow-up experiments assessing the dose-dependent response of CCL3 in wild-type hosts. 200 ng, 2 µg, and 20 µg/mouse were administered intravenously 12 hours following Td pre-conditioning and 12 hours prior to the DC vaccine.

Results:

Exogenous administration of CCL3 could rescue the limited DC migration in Ccl3−/− mice, but only when the Td recall responses were induced (FIG. 3g), indicating that the ability of Td pre-conditioning to increase DC migration to VDLNs was dependent on both CD4+ recall responses and host-derived CCL3.

Alterations in CCL21 expression along the lymphatic endothelium in the skin take place in the context of inflammation and have been associated with increased DC migration8. Following Td pre-conditioning, higher levels of CCL21 were seen in Td-treated wild-type mice compared to Ccl3−/− mice, and exogenous administration of CCL3 rescued the diminished levels of CCL21 at the vaccine sites of Ccl3−/− mice only in the context of Td recall responses (FIG. 3h). Therefore, the ability of Td pre-conditioning to induce CCL21 levels at the vaccine site was dependent on both CD4+ recall responses and host-derived CCL3. Furthermore, Td pre-conditioning resulted in an increase in CCL21 in inguinal lymph nodes both ipsilateral and contralateral to the side of Td pre-conditioning (FIG. 3i). CCL21 expression in the VDLNs of Td-treated Ccl3−/− mice was expressed at levels lower than that of wild-type Td pre-conditioned mice. However, reconstitution of CCL3 back into Ccl3−/− mice significantly increased the expression of CCL21 in VDLNs, but only in the context of competent Td recall responses (FIG. 3j).

Significance of CCL21:

Alterations in CCL21 expression along the lymphatic endothelium in the skin take place in the context of inflammation and have been associated with increased DC migration.[8] This is the key homing chemokine that facilitates DC entry into lymphatic vessels and draining lymph nodes. Prior studies have demonstrated that migration of mature DCs to VDLNs is regulated at the point of entry in tissue lymphatic vessels. Tissue-derived DCs will follow CCL21 gradients into initial afferent lymphatic vessels, which subsequently channel DCs into the subcapsular sinus of draining lymph nodes. We investigated whether increased DC migration to VDLNs following Td pre-conditioning could be a result of elevated CCL21 in the skin, thus facilitating DC entry into afferent lymphatic vessels. Following Td pre-conditioning, we found skin-derived CCL21 to be expressed at higher levels in Td-treated WT mice compared to Ccl3−/− mice (FIG. 3h). In parallel to our findings of DC migration (FIG. 3g) and CCL21 levels in the draining lymph nodes (FIG. 3j), we found that CCL21 expression in the skin could be significantly increased in Ccl3−/− mice with Td recall responses and exogenous CCL3. Increased CCL21 expression in the skin may facilitate initial DC entry into afferent lymphatics and subsequent trafficking into VDLNs. These results suggest that increased DC migration to VDLNs following Td pre-conditioning could be mediated through the induction of CCL21 and that CCL3 may be involved in enabling this step. However, it remains possible that additional mechanisms could also contribute to the increased DC accumulation in VDLNs.

REFERENCES

The disclosure of each reference cited is expressly incorporated herein as is the disclosure of any priority application to which benefit is claimed, including, but not limited to U.S. Ser. No. 61/904,250.

1. Steinman, R. M. & Banchereau. J. Taking dendritic cells into medicine. *Nature* 449, 419-426 (2007).
2. Palucka, A. K., et al. Spontaneous proliferation and type 2 cytokine secretion by CD4+T cells in patients with metastatic melanoma vaccinated with antigen-pulsed dendritic cells. *J Clin Immunol* 25, 288-295 (2005).
3. Palucka, A. K., et al. Single injection of CD34+ progenitor-derived dendritic cell vaccine can lead to induction of T-cell immunity in patients with stage IV melanoma. *J. Immunother* 26, 432-439 (2003).
4. Palucka, A. K., et al. Dendritic cells loaded with killed allogeneic melanoma cells can induce objective clinical responses and MART-1 specific CD8+ T-cell immunity. *J Immunother* 29, 545-557 (2006).
5. Palucka, K. & Banchereau, J. Cancer immunotherapy via dendritic cells. *Nat Rev Cancer* 12, 265-277 (2012).
6. Liau, L. M., et al. Dendritic cell vaccination in glioblastoma patients induces systemic and intracranial T-cell responses modulated by the local central nervous system tumor microenvironment. *Clin Cancer Res* 11, 5515-5525 (2005).
7. Yu, J. S., et al. Vaccination with tumor lysate-pulsed dendritic cells elicits antigen-specific, cytotoxic T-cells in patients with malignant glioma. *Cancer Res* 64, 4973- (2004).
8. Martin-Fontecha, A., et al. Regulation of dendritic cell migration to the draining lymph node: impact on T lymphocyte traffic and priming. *J Exp Med* 198, 615-621, 23 Aug. 2018. (2003).
9. Dziurzynski, K., et al. Consensus on the role of human cytomegalovirus in glioblastoma. *Neuro Oncol* 14, 246-255 (2012).
10. Ranganathan, P., Clark, P. A., Kuo, J. S., Salamat, M. S. & Kalejta, R. F. Significant association of multiple human cytomegalovirus genomic Loci with glioblastoma multiforme samples. *J Virol* 86, 854-864 (2012).
11. Mitchell. D. A., et al. Sensitive detection of human cytomegalovirus in tumors and peripheral blood of patients diagnosed with glioblastoma. *Neuro Oncol* 10, 10-18 (2008).
12. Cobbs. C. S., et al. Human cytomegalovirus infection and expression in human malignant glioma. *Cancer Res* 62, 3347-3350 (2002).
13. Myers, M. G., Beckman, C. W., Vosdingh, R. A. & Hankins, W. A. Primary immunization with tetanus and diphtheria toxoids. Reaction rates and immunogenicity in older children and adults. *JAMA* 248, 2478-2480 (1982).

14. Stupp, R., et al. Radiotherapy plus Concomitant and Adjuvant Temozolomide for Glioblastoma. *N Engl J Med* 352, 987-996 (2005).
15. Curran, W. J., Jr. et al. Recursive partitioning analysis of prognostic factors in three Radiation Therapy Oncology Group malignant glioma trials. *J Natl Cancer Inst* 85, 704-710 (1993).
16. Gorlia, T., et al. Nomograms for predicting survival of patients with newly diagnosed glioblastoma: prognostic factor analysis of EORTC and NCIC trial 26981-22981/CE.3. *Lancet Oncol* 9, 29-38 (2008).
17. Nakano, H. & Gunn, M. D. Gene duplications at the chemokine locus on mouse chromosome 4: multiple strain-specific haplotypes and the deletion of secondary lymphoid-organ chemokine and EBI-1 ligand chemokine genes in the plt mutation. *J Immunol* 166, 361-369 (2001).
18. Zhang, Y., et al. Mobilization of dendritic cell precursors into the circulation by administration of MIP-1alpha in mice. *J Natl Cancer Inst* 96, 201-209 (2004).
19. He, S., et al. MIP-3alpha and MIP-1alpha rapidly mobilize dendritic cell precursors into the peripheral blood. *J Leukoc Biol* 84, 1549-1556 (2008).
20. Castellino, F., et al. Chemokines enhance immunity by guiding naive CD8+ T cells to sites of CD4+ T cell-dendritic cell interaction. *Nature* 440, 890-895 (2006).
21. McLendon, R E., et al. Immunohistochemical detection of the DNA repair enzyme O6-methylguanine-DNA methyltransferase in formalin-fixed, paraffin-embedded astrocytomas. *Lab Invest.* 78, 643-644 (1998).
22. Romani, N., et al. Proliferating dendritic cell progenitors in human blood. *J Exp Med* 180, 83-93 (1994).
23. Nair, S., Archer, G. E. & Tedder, T. F. Isolation and generation of human dendritic cells. Vol. 99 1-23 (Current Protocols in Immunology, 2012).
24. Thumer, B., et al. Generation of large numbers of fully mature and stable dendritic cells from leukapheresis products for clinical application. *J. Immunol Methods.* 223, 1-15 (1999).
25. Therasse, P., et al. New guidelines to evaluate the response to treatment in solid tumors. European Organization for Research and Treatment of Cancer, National Cancer Institute of the United States. National Cancer Institute of Canada. *J Natl Cancer Inst* 92, 205-216 (2000).
26. Nakano, H., et al. Blood-derived inflammatory dendritic cells in lymph nodes stimulate acute T helper type 1 immune responses. *Nat Immunol* 10, 394-402 (2009).
27. Sanchez-Perez, L., et al. Potent selection of antigen loss variants of B16 melanoma following inflammatory killing of melanocytes in vivo. *Cancer Res* 65, 2009-2017 (2005).
28. Daniels, G. A., et al. A simple method to cure established tumors by inflammatory killing of normal cells. *Nat Biotechnol* 22, 1125-1132 (2004).
29. Fidler, I. J. Biological behavior of malignant melanoma cells correlated to their survival in vivo. *Cancer Res.* 35, 218-224 (1975).
30. Schumann, K., et al. Immobilized chemokine fields and soluble chemokine gradients cooperatively shape migration patterns of dendritic cells. *Immunity* 32, 703-713 (2010).

We claim:

1. A method of immunizing a human, comprising: administering a first acellular immunogen to the human; and administering a second immunogen to the human, whereby administration of the first immunogen increases migration of the second immunogen to vaccine draining lymph nodes (VDLNs), wherein the first acellular immunogen is not an inflammatory cytokine, wherein the first and second immunogens are distinct, wherein the human has been previously immunized with or exposed to the first immunogen, wherein the human has memory T cells which are specific and responsive to the first immunogen, and wherein the first and second administrations are separated by 1 hour to 4 weeks.

2. The method of claim 1 wherein the first immunogen is selected from the group consisting of tetanus toxoid, diphtheria toxoid, tetanus and diphtheria toxoids, pneumococcal conjugate vaccine (PCV), and haemophilus b conjugate vaccine.

3. The method of claim 1 wherein the first and second administrations are separated by 6 to 72 hours.

4. The method of claim 1 wherein the first and second administrations are separated by 24 to 48 hours.

5. The method of claim 1 wherein the first immunogen induces production of CCL3.

6. The method of claim 1 wherein the first immunogen expands $CD4^+$ T cell memory.

7. The method of claim 1 wherein the second immunogen comprises a tumor-associated or tumor-specific antigen or peptide.

8. The method of claim 1 wherein the second immunogen comprises an antigen of an infectious agent.

9. The method of claim 1 wherein the second immunogen comprises a dendritic cell vaccine.

10. The method of claim 1 wherein the second immunogen comprises an antigen-pulsed dendritic cell vaccine.

11. The method of claim 1 wherein the second immunogen comprises dendritic cells pulsed with a CMV integument protein pp65 RNA.

12. The method of claim 1 wherein the human has a cancer.

13. The method of claim 1 wherein the human has a glioblastoma multiforme.

14. The method of claim 1 wherein the human has an infectious disease.

15. The method of claim 1 wherein the first immunogen comprises a fusion protein of tetanus toxoid and chemokine (C-C motif) ligand 3 (CCL3).

16. The method of claim 1 wherein the first immunogen comprises a fusion protein of diphtheria toxoid and chemokine CCL3.

17. The method of claim 1 wherein the step of administering the first or second immunogen is performed intradermally.

18. The method of claim 1 wherein the human has a tumor.

19. The method of claim 1 wherein the human has a microbial infection.

20. The method of claim 1 wherein the human has a viral infection.

21. The method of claim 1 wherein the first and second administrations are separated by up to 7 days.

22. The method of claim 1 wherein the second immunogen comprises CMV integument protein pp65.

23. The method of claim 1 wherein the second immunogen comprises a bacterial protein or RNA.

24. The method of claim 1 wherein the second immunogen comprises a parasite protein or RNA.

25. The method of claim 1 wherein the second immunogen comprises a fungal protein or RNA.

26. The method of claim 1 wherein the human has breast cancer.

27. The method of claim 1 wherein the human has colorectal cancer.

28. The method of claim 1 wherein the human has prostate cancer.

29. The method of claim 7 wherein the human has a cancer.

30. The method of claim 7 wherein the human has a glioblastoma multiforme.

31. The method of claim 8 wherein the human has an infectious disease.

* * * * *